(12) United States Patent
Mueller-Auffermann

(10) Patent No.: US 12,344,828 B2
(45) Date of Patent: *Jul. 1, 2025

(54) CELL-BASED MEAT PRODUCTS AND CELL BIOMASSES WITH CELLS CULTIVATED IN A FILTER CAKE

(71) Applicant: Upside Foods, Inc., Berkeley, CA (US)

(72) Inventor: Konrad Mueller-Auffermann, Emeryville, CA (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/542,048

(22) Filed: Dec. 15, 2023

(65) Prior Publication Data

US 2024/0117287 A1 Apr. 11, 2024

Related U.S. Application Data

(63) Continuation of application No. 17/656,986, filed on Mar. 29, 2022, now Pat. No. 11,891,596, which is a
(Continued)

(51) Int. Cl.
*C12M 1/12* (2006.01)
*C12M 1/00* (2006.01)
*C12M 1/33* (2006.01)

(52) U.S. Cl.
CPC ............ *C12M 25/02* (2013.01); *C12M 29/10* (2013.01); *C12M 45/02* (2013.01)

(58) Field of Classification Search
CPC ...... C12M 25/02; C12M 25/14; C12M 25/18; C12M 29/10; C12M 29/04; C12M 41/40;
(Continued)

(56) References Cited

U.S. PATENT DOCUMENTS

| 5,501,971 A | 3/1996 | Freedman et al. |
| 8,703,216 B2 * | 4/2014 | Forgacs ............... C12N 5/0062 426/55 |

(Continued)

FOREIGN PATENT DOCUMENTS

| JP | 2019-068760 A | 5/2019 |
| KR | 10-2013-0110144 A | 10/2013 |

(Continued)

OTHER PUBLICATIONS

Extended European Search Report as received in EP application 22873757.3 dated Jun. 24, 2024.
(Continued)

*Primary Examiner* — Michael L Hobbs
(74) *Attorney, Agent, or Firm* — Keller Preece PLLC

(57) ABSTRACT

Provided herein are filter cake-based systems and methods for cultivating cells and cell biomass therefrom. Provided herein is a system for cultivating cells and cell biomass comprising a filter chamber comprising at least one inlet and at least one outlet, at least one filter support located within the filter chamber, and a filter cake located on the filter support, wherein the filter cake comprises at least one filter aid and a plurality of cells. Provided herein is a method for optimizing the cultivation of cells and cell biomass, comprising providing a filter support, adding at least one filter aid to the filter support, adding a plurality of cells to the filter aid, wherein the cells and the filter aid together comprise a filter cake, growing the cells into a cell biomass in the filter cake, wherein the filter cake is at least partially compressible.

20 Claims, 19 Drawing Sheets

Related U.S. Application Data continuation of application No. 17/481,176, filed on Sep. 21, 2021, now Pat. No. 11,319,520.

(58) Field of Classification Search
CPC .......... C12M 25/08; C12N 5/0658; C12N 2502/1323; C12N 2511/00; C12N 2521/00; C12N 5/0068; C12N 5/0062; C12N 2533/30; C12N 2535/10; C12N 2501/999; A23L 13/00

See application file for complete search history.

(56) References Cited

U.S. PATENT DOCUMENTS

| | | | | |
|---|---|---|---|---|
| 9,101,093 | B2* | 8/2015 | Chance | A01G 7/02 |
| 11,319,520 | B1* | 5/2022 | Mueller-Auffermann | C12N 5/0658 |
| 11,891,596 | B2* | 2/2024 | Mueller-Auffermann | A23L 13/00 |
| 2005/0244943 | A1 | 11/2005 | Ladisch et al. | |
| 2009/0304677 | A1 | 12/2009 | Ichim et al. | |
| 2014/0248698 | A1 | 9/2014 | Kotera et al. | |
| 2020/0056144 | A1 | 2/2020 | Castillo et al. | |
| 2020/0080050 | A1* | 3/2020 | Nahmias | C12M 21/00 |
| 2020/0224144 | A1 | 7/2020 | Love et al. | |
| 2020/0248120 | A1 | 8/2020 | Ferrie et al. | |
| 2021/0145031 | A1 | 5/2021 | Leung et al. | |
| 2022/0195359 | A1* | 6/2022 | Lavon | C12M 41/26 |

FOREIGN PATENT DOCUMENTS

| | | |
|---|---|---|
| WO | 2013/058403 A1 | 4/2013 |
| WO | 2015/130222 A1 | 9/2015 |
| WO | 2018/170139 A1 | 9/2018 |
| WO | 2021/108093 A1 | 6/2021 |
| WO | 2021/111270 A1 | 6/2021 |

OTHER PUBLICATIONS

Notice of Acceptance as received in AU 2024202654 dated Jun. 4, 2024.

Office Action as received in CN application 202280029807.0 dated Jul. 16, 2024.

Notice of Allowability as received in IL application 308441 dated May 9, 2024.

International Preliminary Report on Patentability as received in PCT/US2022/071418, dated Apr. 4, 2024.

Notice of Acceptance received in AU application 2022349541, dated Jan. 8, 2024.

Office Action as received in CN application 202280029807.0, dated Feb. 21, 2024.

International Search Report & Written Opinion as received in PCT/US2022/071418 dated Jul. 8, 2022.

Examination Report as received in AU application 2022349541 dated Nov. 9, 2023.

Examination Report as received in CA application 3,219,050 dated Nov. 24, 2023.

U.S. Appl. No. 17/481,176, filed Jan. 12, 2022, Office Action.

U.S. Appl. No. 17/481,176, filed Mar. 15, 2022, Notice of Allowance.

U.S. Appl. No. 17/656,986, filed Jul. 6, 2023, Office Action.

U.S. Appl. No. 17/656,986, filed Oct. 5, 2023, Notice of Allowance.

Notice of Allowability as received in IL application 314595 dated Sep. 23, 2024.

Office Action as received in JP Application 2023-570447 dated Sep. 17, 2024.

Final Rejection as received in JP Application 2023-570447 dated Feb. 28, 2025.

Written Opinion and Search Report as received in SG application 11202307384P dated Feb. 3, 2025.

\* cited by examiner

CELL-BASED MEAT PRODUCTS AND CELL BIOMASSES WITH CELLS CULTIVATED IN A FILTER CAKE

CROSS-REFERENCE TO RELATED APPLICATIONS

This application is a continuation of U.S. application Ser. No. 17/656,986, filed Mar. 29, 2022, which is a continuation of U.S. application Ser. No. 17/481,176, filed on Sep. 21, 2021, now U.S. Pat. No. 11,319,520. Each of the aforementioned applications are hereby incorporated by reference in their entirety.

BACKGROUND

Bringing cell-based meat produced by culturing metazoan cells to the marketplace requires overcoming several hurdles. For example, the cultivation of thick cell-based meat products at large scale can be impeded by inefficient and suboptimal culturing of cells and tissues. As a result, the harvested yield and quality may be reduced, necessitating the addition of synthetic ingredients, resulting in an increase in cost and presence of undesirable additives.

Provided herein are systems and methods for the optimal cultivation of cell-based meat, as well as other tissue-based applications.

SUMMARY

Provided herein are filter cake-based systems and methods for cultivation of cells and cell biomass.

Some embodiments disclosed herein provide a method for optimizing the cultivation of cells and cell biomass, the method comprising providing a filter support, adding at least one filter aid to the filter support, adding a plurality of cells to the filter aid, wherein the cells and the filter aid together comprise a filter cake, growing the cells into a cell biomass in the filter cake, wherein the filter cake is at least partially compressible. In some embodiments, the cell biomass is a meat product.

In some embodiments, the method comprises compressing or decompressing the filter cake by varying one or more of flow rate and pressure. In some embodiments, the filter cake is edible. In some embodiments, the filter aid is edible or degradable. In some embodiments, the filter aid comprises at least one compressible filter aid and at least one non-compressible filter aid. In some embodiments, the filter aid is at least partially compressible.

In some embodiments, the filter aid comprises organic fibers of a length of between about 1 μm-about 20 μm, about 20 μm-about 50 μm, about 50 μm-about 80 μm, about 80 μm-about 110 μm, about 110 μm-about 140 μm, about 140 μm-about 170 μm, about 170 μm-about 200 μm, about 200 μm-about 230 μm, about 230 μm-about 260 μm, about 260 μm-about 290 μm, or about 290 μm-about 320 μm. In some embodiments, the filter aid comprises organic fiber with a fiver titer of between about 0.01 dtex-about 120 dtex, about 0.05 dtex-about 60 dtex, about 0.1 dtex-about 30 dtex, about 0.2 dtex-about 15 dtex, or about 0.5 dtex-about 5 dtex. In some embodiments, the filter aid is added to the filter support at between about 25 g/m$^2$-about 12000 g/m$^2$, about 50 g/m$^2$ about 6000 g/m$^2$, about 100 g/m$^2$-about 3000 g/m$^2$, about 200 g/m$^2$-about 1500 g/m$^2$, or about 400 g/m$^2$-about 750 g/m$^2$.

In some embodiments, the filter support is comprised in a horizontal filter, vertical filter, plate filter, plate press filter, mash filter, cloth filter, mass filter or candle filter. In some embodiments, the temperature is maintained at between about 10° C. to about 45° C. during growth. In some embodiments, the cells are from a species of poultry, game, aquatic or livestock.

Provided herein are methods for establishing perfusion through a growing cell biomass. In some embodiments, the method comprises seeding cells on an at least partially compressible filter aid, compressing the cells, the at least partially compressible filter aid, or both, flowing media through the at least partially compressible filter aid to grow the cells into a cell biomass, whereby growth reduces perfusion over time, decompressing the cells, the at least partially compressible filter aid, or both, to increase perfusion of media. In some embodiments, the cell biomass is compressed by a fluid pressure or flow of the media. In some embodiments, the cell culture media provides nutrients and oxygenation to promote cell growth. In some embodiments, the cell biomass is decompressed with a relief valve, a lower pressure media flow, flow reduction of the media, or some combination thereof. In some embodiments, the cell biomass, its substrate, or both are decompressed proportionally to the growth of the cell mass, whereby perfusion is stabilized. In some embodiments, the cell biomass, the at least partially compressible filter aid, or both cycle between a compressed state and a decompressed state at a pulsing frequency. In some embodiments, the pulsing frequency is between about 20 seconds to about 20 minutes.

DETAILED DESCRIPTION

Figure 1A:
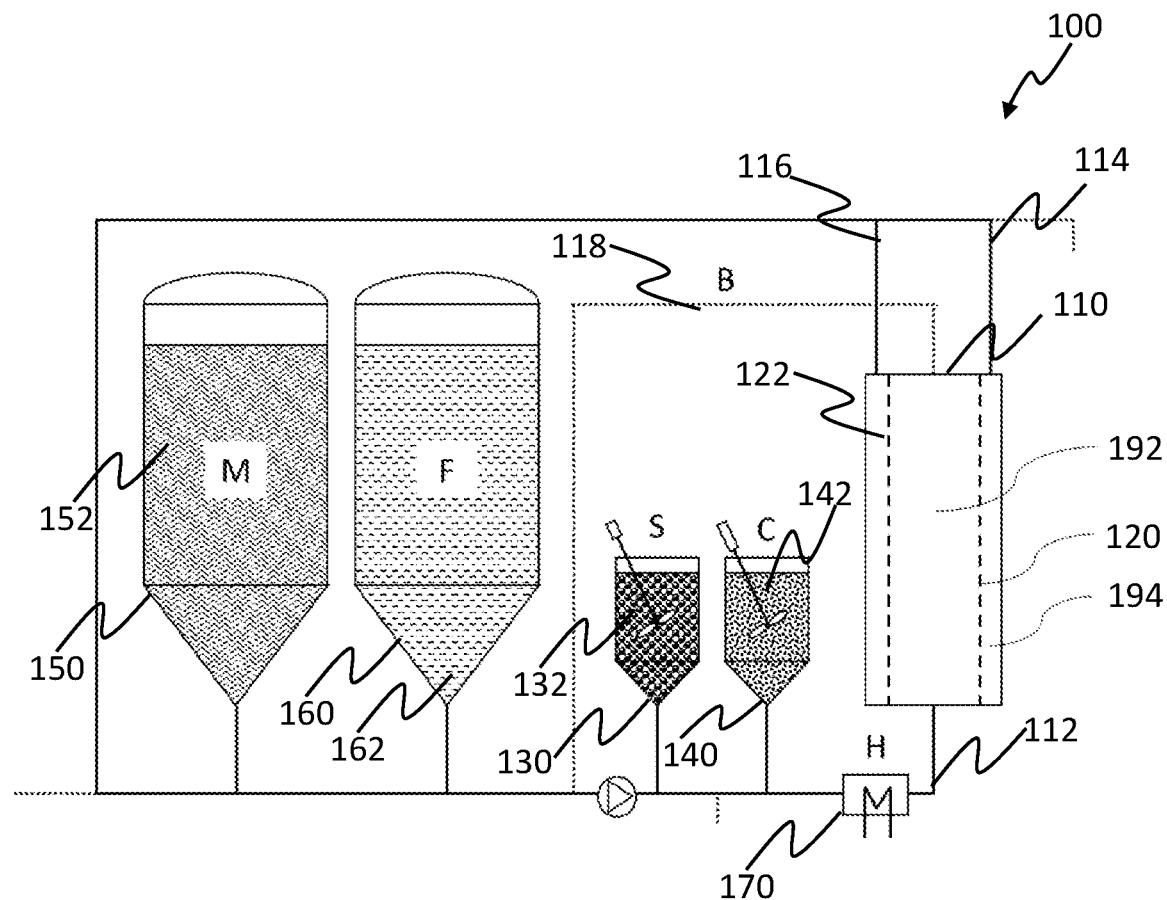
FIG. 1A depicts an illustrative schematic of an exemplary system and method of the disclosure for cultivating cells. The exemplary system shown in FIG. 1A includes a filter chamber containing filter supports in fluidic communication with two filter aid chambers, containing exemplary fibrous plant-based filter aids (starch and cellulose), and two cell tanks containing exemplary cells (myoblasts and fibroblasts), respectively.

Before describing particular embodiments in detail, it is to be understood that the disclosure is not limited to the particular embodiments described herein, which can vary. It is also to be understood that the terminology used herein is for the purpose of describing particular illustrative embodiments only and is not intended to be limiting unless otherwise defined. The terms used in this specification generally have their ordinary meaning in the art, within the context of this disclosure and in the specific context where each term is used. Certain terms are discussed below or elsewhere in the specification, to provide additional guidance to the practitioner in describing the compositions and methods of the disclosure and how to make and use them. The scope and meaning of any use of a term will be apparent from the specific context in which the term is used. As such, the definitions set forth herein are intended to provide illustrative guidance in ascertaining particular embodiments of the disclosure, without limitation to particular compositions or biological systems.

Standard techniques may be used for recombinant DNA, tissue culture, and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery.

As used in the present disclosure and the appended claims, the singular forms "a," "an" and "the" include plural references unless the content clearly dictates otherwise.

Throughout the present disclosure and the appended claims, unless the context requires otherwise, the word "comprise," or embodiments such as "comprises" or "comprising," will be understood to imply the inclusion of a stated element or group of elements but not the exclusion of any other element or group of elements.

As used in the present disclosure the term "about" shall generally mean an acceptable degree of error for the quantity measured. Exemplary degrees of error are within 20%, within 10%, and within 5% of a value or range of values.

Cultivation of cells dispersed in suspension typically limits their assembly into higher order structures, such as tissues and organs. Thus, their use may not be optimal for several applications, including the production of cell-based meat, cultivation of stem cells, liver cells, cell spheroids, nodules, organoids, artificial organs, 3D cell culture, bio-fabrication, regenerative bio-engineering, and the like. Cells grown in suspension do not typically form significant interconnections with each other. The few smaller cell-clusters or pellets that do form may not grow significantly and may be unable to fuse and form cross-linked multi-nuclei higher-order tissue assemblies, such as muscle fibers. As this is important for the large-scale manufacturing and consistency of cell sheets, inclusive of cell-based meat products, the cells are either separated in further processing steps (e.g. centrifugation) and mixed with other substances to a semi-finished or finished product, or are adhered on to a surface, (e.g. by sedimentation) to form thin tissue layers. However, both these methods are often suboptimal and inefficient. If the individual cells are separated without significant tissue formation, additives (such as enzymes and/or fibers) are typically used for texturing, which remain at least partially in the cell-based meat, raising quality, batch-to-batch variability, and safety concerns. Further, since the cells are no longer actively supplied with oxygen and nutrients under these conditions, they may quickly lyse, inhibiting any further increase in cell biomass or even cell fusion. If the cells are adhered to a surface, a tissue layer formed by cross-linking, cell fusion and cell biomass increase may be formed. However, because the growing tissue increasingly hinders the diffusion of nutrients and oxygen into deeper layers, the viable tissue thickness is severely limited, and often results in lysing of cells in the lower boundary layers towards the supporting structure. This limitation of non-homogeneous cell and tissue culture is also seen with cultivation procedures using matrix structures, such scaffolds, to increase the surface area of adhesion. Provided herein are systems and methods for cultivation of cells that overcome the above-mentioned drawbacks.

Described herein are systems and methods in which cells in suspension are added and cultured using filtration in a filter cake. As used herein, a filter cake comprises a plurality of cells and at least one filter aid. The filter cake may be located on a filter support. Without being bound to theory or mechanism, in some embodiments, the filtration flow guides the free-floating dispersed suspension cells to a compact filter cake for cultivation. The flowing media allows for perfusion of the cells in the filter cake, providing essential nutrients and oxygen under sterile conditions, enabling cell growth, cell division, cell fusion, and cross-linking Cellular waste products are also actively eliminated by the flow. Adequate and homogeneous supply of growth essential nutrients and gases reaching even the growing cells in deeper layers. Thus, the cells in the filter cake form thick robust tissues and higher order cell biomass assemblies (e.g. fusion of myoblasts into multi-nucleated myotubes). Properties of the filter cake, such as porosity, permeability, compressibility, can be individually tuned according to the specific needs of the cells/cell biomass, by adjusting parameters such as the flow volume per time, the flow direction, and/or the pressure. Mixtures of different cell types and/or filter aids can be used to create specific structural and process influencing features in the filter cake, thus, overall efficiency of producing cell-based meat is dramatically improved, bringing down costs These systems and methods are applicable not only for the production of cell-based meat, but any other applicable field, such as therapeutics, bio-manufacturing, bio-engineering, cultivation of stem cells, liver cells, cell spheroids, nodules, organoids, artificial organs, 3D cell culture, bio-fabrication, regenerative bio-engineering, and the like.

Filter Cake-Based Systems for Cultivating Cells and Cell Biomass

Provided herein are filter cake-based systems for cultivating cells and cell biomass. In some embodiments, the system for cultivating cells comprises a filter chamber comprising at least one inlet and at least one outlet, at least one filter support located within the filter chamber, and a filter cake located on the filter support, wherein the filter cake comprises at least one filter aid and a plurality of cells.

Figure 1B:
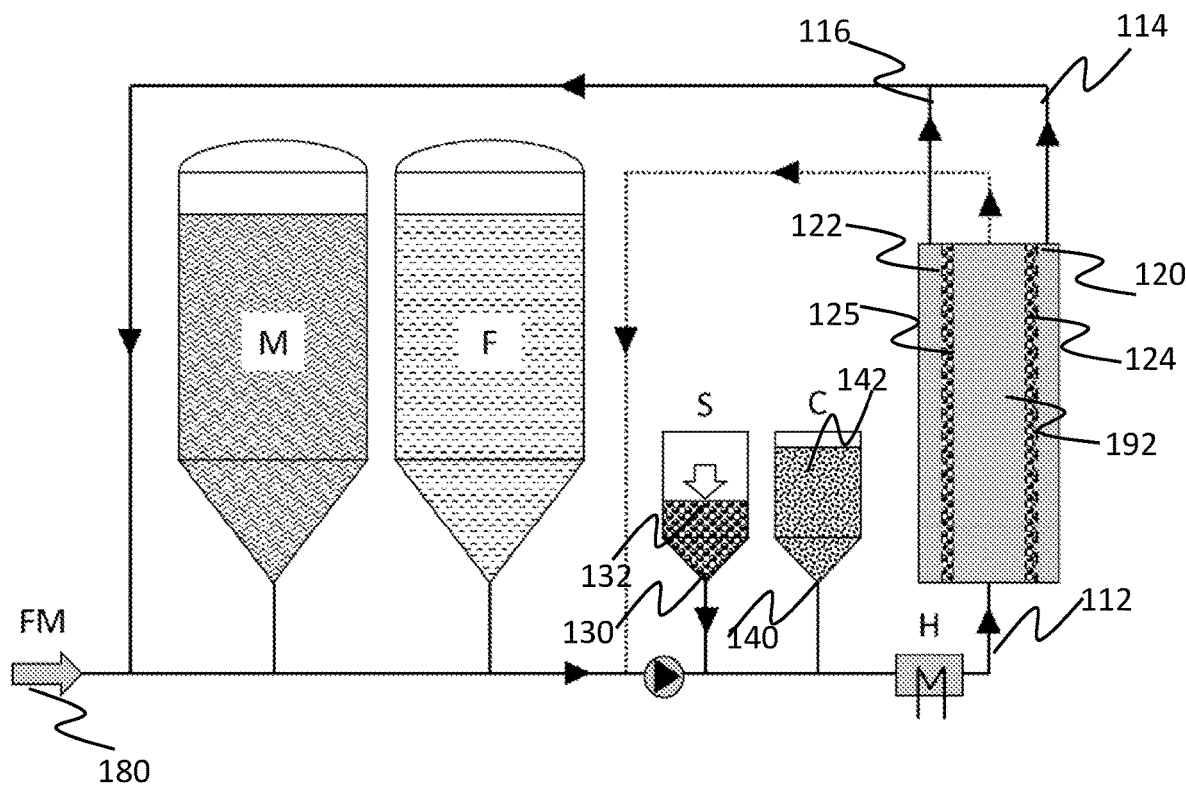
FIG. 1B depicts an exemplary embodiment of adding a filter aid to filter supports to form pre-coat layers.
Figure 1C:
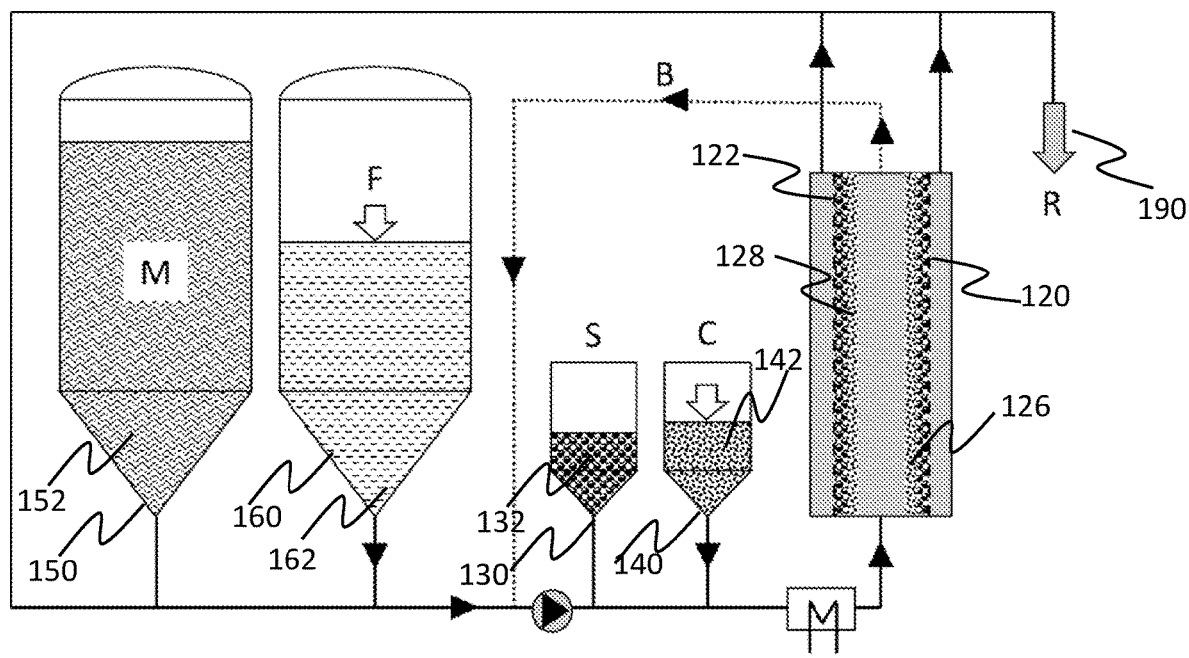
FIG. 1C depicts an exemplary embodiment of adding cells and/or filter aids on to filter supports to form filter cakes.
Figure 1D:
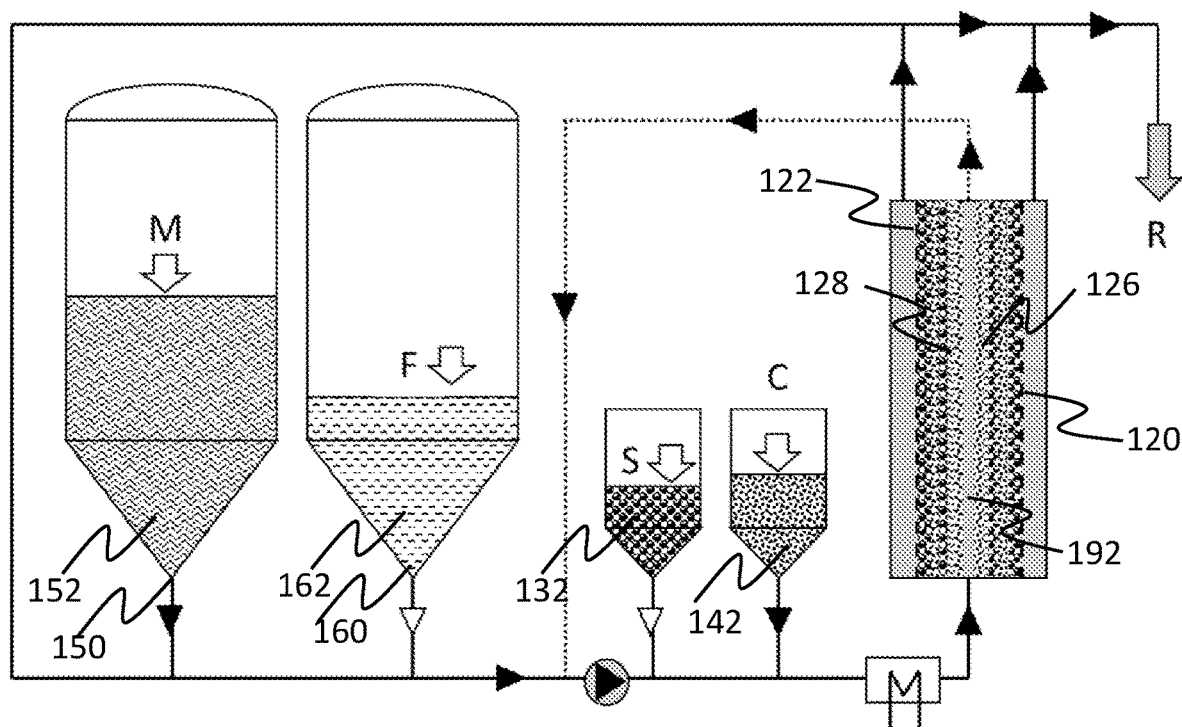
FIG. 1D depicts another exemplary embodiment of adding cells and/or filter aids on to filter supports to form filter cakes.

FIG. 1A shows an exemplary system 100 of the present disclosure. System 100 may comprise a filter chamber 110 with an inlet 112, two outlets 114 and 116, and a bypass (B) outlet 118. The filter chamber may be divided by the filter support into unfiltered (also referred to as unfiltrate or non-filtered) chamber 192 and filtered (also referred to as filtrate) chamber 194. In this exemplary system, two filter supports, 120 and 122 may be located within the filter chamber 110. In alternative embodiments, the filter chamber may include as many as hundreds of filter supports to support substantial and robust cell growth. Filter aids 132 and 142 may be stored in the filter aid chambers 130 and 140, respectively. In some embodiments the filter aid may be a plant-based fiber. In some embodiments, the filter aid 132 may be (native) starch (S) and 142 may be cellulose (C). Cells, such as myoblasts and fibroblasts, may be stored in one or more cell tanks (150 and 160). As shown in FIG. 1A, myoblasts (M) 152 and fibroblasts (F) 162 may be stored in the cell tanks 150 and 160, respectively. The filter aid chambers 130 and 140, the cell tanks 150 and 160, and the filter chamber 110 may be in fluidic communication with each other. A heat exchanger 170 (H) may be used to regulate the temperature of the filter chamber. As shown in FIG. 1D, filter cakes 126 and 128, comprised of the filter aids (starch (132) and cellulose (142)), and cells (myoblasts (152) and fibroblasts (162)) may form on the filter supports.

Cells and Cell Biomass

The cells and cell biomass thereof used in the systems and methods described herein may be produced by the in vitro culturing of naturally occurring, genetically engineered, or otherwise modified cells in culture.

The systems and methods provided herein are applicable to any metazoan cell in culture. In some embodiments, in the context of using the systems and methods of the disclosure to generate cell-based meat, the cells are from any metazoan species whose tissues are suitable for dietary consumption. In some embodiments, the cells may demonstrate a capacity for differentiation into mature tissue, such as skeletal muscle tissue, other muscle tissues, or any cell, cellular biomass, and/or tissue that can be consumed as cell-based meat or nutrients thereof. The cells in the present disclosure may be primary cells, or cell lines. The cells may be adherent-cells or non-adherent cells, flocculating or non-flocculating cells.

In some embodiments, the cells are derived from any non-human animal species intended for human or non-human dietary consumption (e.g. cells of avian, ovine, caprine, porcine, bovine, piscine origin), cells of livestock, poultry game, or aquatic species, etc.).

In some embodiments, the cells are from livestock such as domestic cattle, pigs, sheep, goats, camels, water buffalo, rabbits, and the like. In some embodiments, the cells are from poultry such as domestic chicken, turkeys, ducks, geese, pigeons, and the like. In some embodiments, the cells are from game species such as wild deer, gallinaceous fowl, waterfowl, hare, and the like. In some embodiments, the cells are from aquatic species or semi-aquatic species harvested commercially from wild fisheries or aquaculture operations, or for sport, including certain fish, crustaceans, mollusks, cephalopods, cetaceans, crocodilians, turtles, frogs, and the like.

In some embodiments, the cells are from exotic, conserved, or extinct animal species. In some embodiments, the cells are from *Gallus gallus, Gallus domesticus, Bos taurus, Sous scrofa, Meleagris gallopavo, Anas platyrynchos, Salmo salar, Thunnus thynnus, Ovis aries, Coturnix coturnix, Capra aegagrus hircus,* or *Homarus americanus.* Accordingly, exemplary cell-based meat products of the disclosure include avian meat products, chicken meat products, duck meat products, and bovine meat products.

In some embodiments, the cells are primary stem cells, self-renewing stem cells, embryonic stem cells, pluripotent stem cells, induced pluripotent stem cells, or differentiated progeny of stem cells.

In some embodiments, the cells are modified to differentiate into skeletal muscle tissue, connective tissue, fat tissue, and/or any other mature tissue, e.g. useful for cultured meat production or some other application.

In some embodiments, the cells are myogenic cells, programmed to become muscle, or muscle-like cells. In some embodiments, the myogenic cells are natively myogenic, e.g. myoblasts. Natively myogenic cells include, but are not limited to, myoblasts, myocytes, satellite cells, reserve cells, side population cells, muscle derived stem cells, mesenchymal stem cells, myogenic pericytes, or mesoangioblasts.

In some embodiments, cells are of the skeletal muscle lineage. Cells of the skeletal muscle lineage include myoblasts, myocytes, and skeletal muscle progenitor cells, also called myogenic progenitors that include satellite cells, reserve cells, side population cells, muscle derived stem cells, mesenchymal stem cells, myogenic pericytes, and mesoangioblasts.

In other embodiments, the cells are not natively myogenic (e.g. are non-myogenic cells such as fibroblasts or non-myogenic stem cells that are cultured to become myogenic cells in the cultivation infrastructure).

In some embodiments, the cells of the cellular biomass are somatic cells. In some embodiments, the cells of the cellular biomass are not somatic cells.

In some embodiments, the cells are genetically edited, modified, or adapted to grow without the need of specific ingredients including specific amino acids, carbohydrates, vitamins, inorganic salts, trace metals, TCA cycle intermediates, lipids, fatty acids, supplementary compounds, growth factors, adhesion proteins, and recombinant proteins.

In some embodiments, the cells may comprise any combinations of the modifications described herein.

The cell-based meat of the present disclosure, generated using the cell media formulations provided herein, is suitable for both human and non-human consumption. In some embodiments, the cell-based meat is suitable for consumption by non-human animals, such as domesticated animals. Accordingly, the cell media formulations provided herein support the growth of "pet food", e.g. dog food, cat food, and the like.

In some embodiments, the systems and methods may enable production of thick tissues without the need for an added internal scaffold to support tissue dimensionality.

In some embodiments, the cells may be cultivated for therapeutic, diagnostic, bio-manufacturing, or bio-engineering applications. Examples include, cultivation of stem cells, liver cells, cell spheroids, nodules, organoids, artificial organs, lab-on-a-chip, 3D cell culture, bio-fabrication, regenerative bio-engineering, and the like.

Filter Support

The systems described in this disclosure comprise at least one filter support. In some embodiments the system may comprise a plurality of filter supports. For example, the system may comprise at least 1, 5, 10, 20, 30, 40, 50, 60, 70, 80, 90, 100, 200, 300, 400, 500, 1000, 5000, 10,000, 100,000, or 1,000,000 filter supports.

The filter support may be located within a filter chamber. In some embodiments, the system comprises a plurality of filter supports, for example, the system shown in FIG. 1A contains two filter supports 120 and 122 located within the filter chamber 110. The filter supports may be made of permeable structure like nets, cloughs, mashes, or sintered materials and are oftentimes produced as plates or candles.

In some embodiments the filter support comprises a horizontal filter, vertical filter, plate filter, plate press filter, mash filter, cloth filter, mass filter or a candle filter. In some embodiments, the filter support may be contained or installed in horizontal filters, vertical filters, plate filters, plate press filters, mash filters, cloth filters, or candle filters.

Any suitable and sterilizable filter support known in the art may be used. A person skilled in the art would understand how to identify and use a filter support in the systems disclosed herein.

The filter support may be of any suitable dimension. In some embodiments the filter support has a surface area of between about 1 meter$^2$-about 2000 meter$^2$.

In some embodiments, the filter support is sterilized before use.

Filter Aid

The systems described in this disclosure comprise at least one filter aid. In some embodiments, the filter aid is stored in filter aid chambers in fluidic communication with the filter chamber. For example, the system shown in FIG. 1A contains two filter aids 132 and 142 stored in filter aid chambers 130 and 140 respectively.

In some embodiments, the filter aid may be composed of incompressible materials (also referred to as non-compressible herein), such as starch, diatomaceous earth, perlites, active charcoal and crystals, or compressible materials, such as vegetable fats, waxes, cellulose, fibers, plant fibers, fungal mycelia, algae, naturally occurring fibers, synthetic fibers, inorganic fibers, organic fibers, wood chips, sprouts, husks, organic shells, plant based proteins, or combinations thereof. Any suitable filter aid or combination of filter aids known in the art may be used herein. A person skilled in the art would understand how to identify and use a filter aid in the systems disclosed herein. Combinations of different filter aids with different material properties such as particle sizes, functional surfaces, particle structures, and different compressibility may further be used and combined. For example, combinations of compressible filter aids (e.g. cellulose) and incompressible filter aids (e.g. starch) may be combined at different ratios to form partially compressible filter aids.

The filter aids may be of any suitable length. In some embodiments, the filter aid may have a length of between about 1 μm-about 20 μm, about 20 μm-about 50 μm, about 50 μm-about 80 μm, about 80 μm-about 110 μm, about 110 μm-about 140 μm, about 140 μm-about 170 μm, about 170 μm-about 200 μm, about 200 μm-about 230 μm, about 230 μm-about 260 μm, about 260 μm-about 290 μm, or about 290 μm-about 320 μm. In some embodiments, the filter aid may have a length of no more than about 300 μm. In some embodiments, the filter aid may have a length of between about 20 μm-about 50 μm.

In some embodiments, the filter aid may comprise an organic fiber. In some embodiments, the organic fiber may have a length of between about 1 μm-about 20 μm, about 20 μm-about 50 μm, about 50 μm-about 80 μm, about 80 μm-about 110 μm, about 110 μm-about 140 μm, about 140 μm-about 170 μm, about 170 μm-about 200 μm, about 200 μm-about 230 μm, about 230 μm-about 260 μm, about 260 μm-about 290 μm, or about 290 μm-about 320 μm. In some embodiments, the organic fiber may have a length of no more than about 300 μm. In some embodiments, the organic fiber may have a length of between about 20 μm-about 50 μm.

In some embodiments, the organic fiber may comprise a fiver titer of between about 0.01 dtex-about 120 dtex, about 0.05 dtex-about 60 dtex, about 0.1 dtex-about 30 dtex, about 0.2 dtex-about 15 dtex, or about 0.5 dtex-about 5 dtex.

In some embodiments, the filter aid may be compressible. In some embodiments, at least one of a plurality of filter aids being used may be compressible. In some embodiments, at least one component of the filter aid may be compressible. Non-limiting examples of compressible filter aids or their components include: cellulose, organic fibers, and plant fibers.

In other embodiments, the filter aid may be non-compressible or incompressible. In some embodiments, at least one of a plurality of filter aids being used may be non-compressible. In some embodiments, at least one component of the filter aid may be non-compressible. Non-limiting examples of non-compressible filter aids include: diatomaceous earth, perlites active charcoal, and native starch particles.

In some embodiments, the filter aid may be partially compressible. In some embodiments, a single filter aid may be partially compressible by itself. In some embodiments, one or more compressible filter aids and non-compressible filter aids may be combined to form a partially compressible filter aid.

In some embodiments, the filter aid is compressible by between about 70%-about 75%, about 75%-about 80%, about 80%-about 85%, about 85%-about 90%, about 90%-about 95%, about 95%-about 98%, or about 98%-about 100%.

In some embodiments, a combination of at least one compressible filter aid (CFA) and at least one non-compressible filter aid (NCFA) may be used. In some embodiments, the combination of CFA and NCFA may be between about 70% CFA and about 30% NCFA, about 75% CFA and about 25% NCFA, about 80% CFA and about 20% NCFA, about 85% CFA and about 15% NCFA, about 90% CFA and about 10% NCFA, about 95% CFA and about 5% NCFA, about 98% CFA and about 2% NCFA, or about 99% CFA and about 1% NCFA. In some embodiments, the combination of CFA and NCFA comprises at least about 98% CFA. In some embodiments, the combination of CFA and NCFA may contain no more than about 10%, about 9%, about 8%, about 7%, about 6%, about 5%, about 4%, about 3%, about 2%, about 1%, about 0.5%, about 0.1%, or about 0.01% NCFA. In some embodiments, the combination of CFA and NCFA may contain no more than about 5% NCFA.

In some embodiments, the combination of a CFA and a NCFA may be a ratio of between about 99CFA:1NCFA to about 1CFA:99NCFA. In some embodiments, the combination of a CFA and a NCFA may be a ratio of about 90CFA:10NCFA. In some embodiments, the combination of a CFA and a NCFA may be a ratio of about 95CFA:5NCFA. In some embodiments, the combination of a CFA and a NCFA may be a ratio of about 98CFA:2NCFA.

In some embodiments, the ratio of a CFA to NCFA may be between about 99:1 to about 1:99. In some embodiments, the ratio of a CFA to NCFA may be between about 90:10. In some embodiments, the ratio of a CFA to NCFA may be between about 95:5. In some embodiments, the ratio of a CFA to NCFA may be between about 98:2.

The filter aids may be added in any suitable order. In some embodiments, the filter aids may be added at the same time, sequentially, alternately, or in any relevant order and any time interval.

In some embodiments, the filter aid may be edible. Examples of edible filter aids include fungal mycelia, plant fibers, and cellulose. The use of edible filter aids avoids additional steps required to remove or degrade filter aids during the harvesting step, described below.

In some embodiments, the filter aid may be degradable. Examples of edible filter aids are cellulose, fungal mycelia, algae, plant fibers, starch particles, and plant-based proteins.

In some embodiments, the filter aid may be hollow or otherwise shaped, for example to allow for the homogeneous gaseous (e.g. oxygen) and nutrient supply to the cells being cultivated. Besides hollow, or sectioned fibers, the shape could be L, M, Y, Z, square, round, and/or starshaped in diameters, and straight or cross linked. In some embodiments, the filter aid may be natural or synthetic, in pure form, or with additives, such as coatings. In some embodiments, the filter aid is sterilized before usage.

Filter Chamber

The systems described in this disclosure comprise at least one filter chamber. The filter chamber contains at least one of the filter support(s) described above. In some embodiments, the filter chamber may be divided by the filter support into unfiltered chamber 192, in which the unfiltered fluids, cells and filter aids are introduced, and filtered chamber 194, which is the outlet for the filtered suspensions (FIG. 1A). The filter chamber may have at least one inlet and one outlet and may be in fluidic communication with other components of the system. For example, filter chamber 110 shown in FIG. 1A contains the filter supports 120 and 122, and in fluidic communication via inlet 112 and outlets 114, 116, and bypass outlet 118. The bypass outlet can ensure that the filter cake thickness and cell distribution remain homogeneous over the length of the filter support. In one example, the bypass outlet relieves pressure in the unfiltered chamber and the pressure relief may result in a decompression or relaxation of the filter cake.

The filter chamber may be of any suitable dimension. In some embodiments, the filter chamber has a size of between about 5 liters-about 25,000 liters. In some embodiments, the filter chamber may be a bioreactor.

In some embodiments, the filter chamber may be sterilized. Sterilization may be carried out with any known method, using heat, steam, pressure, irradiation, gases, and/or chemicals.

Filter Cake

The systems described in this disclosure comprise at least one filter cake. The filter cake comprises at least one filter aid and a plurality of cells. In some embodiments, the filter cake is located on the filter support. For example, FIG. 1D shows the filter cakes 126 and 128 formed on the filter supports 120 and 122, respectively, in the unfiltered chamber 192.

One of the advantages of the systems disclosed herein is the ability to customize the properties of the filter cake. This may be achieved, for example, by using the appropriate type of filter aid, adding filter aids added at the same time as cells, sequentially, alternately, or in any relevant order, adding the filter aids accordingly to certain feedbacks like rising differential pressures, and modulating the pressure and flow characteristics of the media.

In some embodiments the filter cake is porous. The permeability of the filter cake can allow for media to actively flow throughout the cake, the cells, and different layers of growing tissue, allowing for nutrients, dissolved oxygen, and growth-relevant substances to penetrate deeply into the filter cake, and undesirable metabolic products to be flushed out. Filter aids with hollow shapes can allow for efficient penetration, especially to deeper lying tissues. Consequently, it is expected that the cells are provided a nutrient rich dynamic surface to adhere, grow, cross-link, and form thick layers of tissues.

Figure 1E:
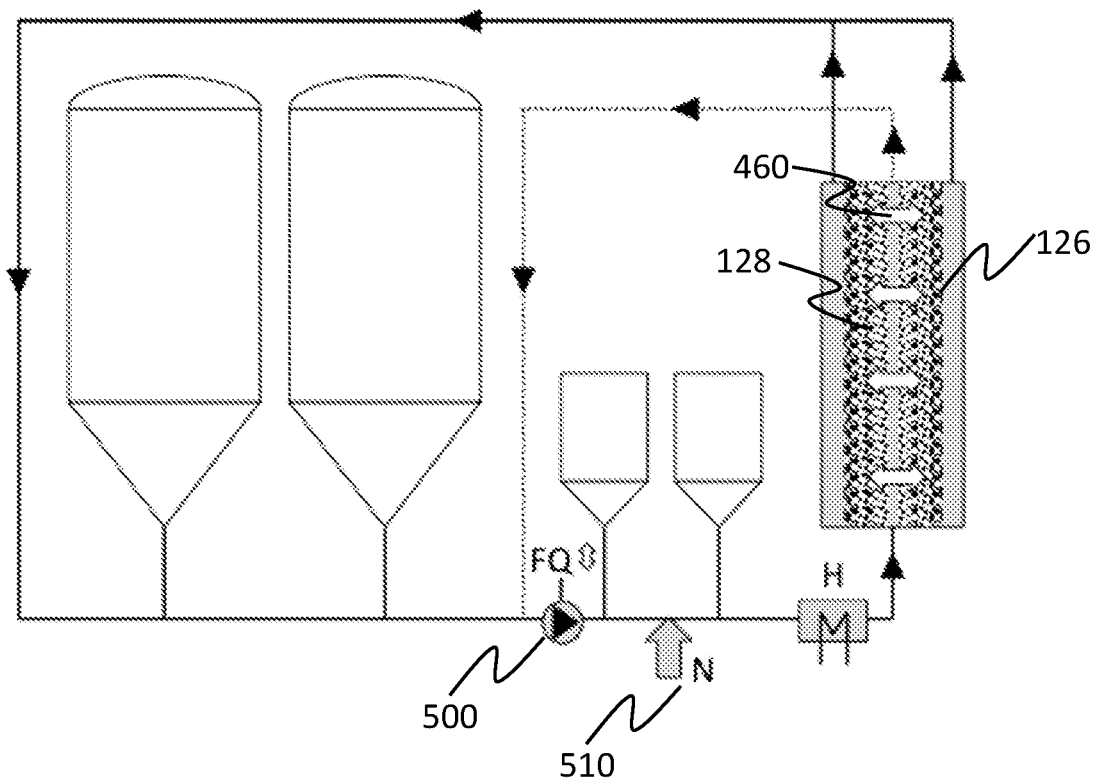
FIG. 1E depicts an exemplary embodiment of compressing and decompressing filter cakes by pressure and/or flow variations.

Based on the type of filter aid used, the filter cake may be compressible or non-compressible. In some embodiments, the filter cake is compressible. For example, filter cakes containing either only compressible filter aids (e.g. cellulose), or compressible filter aids containing little or no non-compressible filters aids (e.g. less than 5%), in addition to cells, would be considered compressible. Periodic pressure and/or flow induced variations between the inlet and outlet may be used to compress and decompress the filter cake intentionally. This tunable compression and decompression of the filter cake is yet another advantage of the systems disclosed herein. This "sponge-like" action, shown by arrows 460 in FIG. 1E for the filter cakes 126 and 128, is expected to enable deeper infiltration of the media and oxygen into the growing layers of cells and tissues, enabling exchange of signaling molecules, and flushing out waste. In some embodiments, the interval-like contraction may achieve a desired stimulation of a tissue being cultivated, e.g. a muscle or muscle-like tissue. The system may comprise a flow control pump 500 (FQ) as shown in FIG. 1E, where the filled in triangle signifies valves and the circle around the filled in triangle signifies a pump. The system may also comprise a nitrogen inlet 510 (N) for drying and/or oxygen displacement (FIG. 1E).

In general, the filter cake is a dynamic structure. As culture media is flowed onto it and through it, the various cells begin to grow and may make connections with neighboring cells, thereby forming a cell biomass. As the cells and the cell biomass grow, the fluid dynamics of the unfiltered chamber to the filtered chamber are in constant flux. Typically, as the cells and the cell biomass grow, the filter cake becomes more dense and less porous. If the flow rate of cell culture media is held constant, despite cell growth, then pressure may build in the unfiltered chamber, thereby leading to further compression of the filter cake and a further decrease in porosity. Left unchecked, a constant flow rate may clog the filter given enough time for robust cell growth. In some instances, the flow rate is reduced to maintain a constant pressure difference between unfiltered chamber and filtered chamber. Such a reduction in flow rate counteracts the resistance increases that result from increasing filter cake thickness. In some embodiments, a computer is configured to control a flow pump and read an unfiltered chamber pressure sensor, whereby the computer can establish and maintain a stable pressure differential between the unfiltered chamber and filtered chamber by taking pressure sensor readings and modulating the flow pump.

In some embodiments, the pressure differential between the unfiltered chamber and filtered chamber are intentionally varied and this variance may be carried out in a repeated or rhythmic fashion. In one example, the filter cake may be periodically compressed and decompressed to maintain the porosity of the filter cake and/or to press the medium sufficiently into the deeper filter cake layers. In this example, the filter cake may exhibit mechanical properties similar to a sponge under the varied pressure. As the pressure is increased, the filter cake is compressed, cells aggregate, porosity decreases, cells are pushed deeper into the filter aids, and cell culture media is ejected through the filter support into the filtered chamber. As the pressure is decreased, the filter cake is decompressed, space opens up around the aggregated cells (e.g. cell mass), porosity increases (thereby allowing cell culture media to perfuse to cells deep in the filter cake), and flow through the filter cake is increased. The compression engagement may be characterized by a rate at which pressure builds and a duration for which a high pressure state is maintained. Likewise, the decompression engagement may be characterized by a rate at which pressure decreases and a duration for which a low pressure state is maintained. The flow of the media may be manipulated to oscillate the filter cake between high pressure and low pressure states at a frequency in a seconds range, a minutes range, an hours range, or in a days range.

In an exemplary embodiment manipulating the pressure differential between the unfiltered chamber and filtered chamber enhances perfusion to cells deep within the filter cake and mitigates the risk of cell death from lack of oxygen or nutrients. In some instances, pressure increases counteract the filter cake's increased resistance to perfusion caused by the growing and expanding cell mass by compressing the cells together, whereby a subsequent pressure decrease results in extra open space around the recently compressed cells where fluid can then freely perfuse.

In some embodiments, the filter cake may be compressed by pressure variations. Any suitable pressure range may be used. In some embodiments, the pressure between the inlet and the outlet is between about 0.01 bar-about 500 bar, about 0.05 bar-about 50 bar, or about 0.1 bar-about 5.0 bar. In some embodiments, the pressure between the inlet and the outlet is between about 0.1-about 5.0 bar.

In some embodiments, the filter cake may be compressed by flow rate variations. Any suitable flow rate may be used. In some embodiments, the flow rate between the inlet and the outlet is between about 0.01 L/min-about 100,000 L/min, about 0.1 L/min-about 10,000 L/min, or about 1 L/min-about 1000 L/min. In some embodiments, the flow rate between the inlet and the outlet is between about 10 L/min-about 1000 L/min.

Another advantage of the systems disclosed herein is the ability to cultivate multiple cell types, in any desired order. For example, the filter cake may contain multiple layers of cell biomass, wherein each layer is of a different cell type, such as alternating layers of myoblasts, adipocytes and fibroblasts. In some embodiments, the filter cake may contain one or more cell types. In some embodiments the filter cake may contain one or more filter aids added in any relevant order. In some embodiments, the filter cake may contain two, three, or more cell types. The plurality of cell types may be added in any relevant order, such as in alternating layers. The filter cake may comprise multiple layers of different cell types and different filter aids.

In some embodiments, the filter cake may contain skeletal muscle cells, stem cells, pluripotent stem cells, embryonic stem cells, induced pluripotent stem cells, fibroblasts, myoblasts, somatic cells, extraembryonic cells, myocytes, satellite cells, side population cells, muscle derived stem cells, mesenchymal stem cells, myogenic pericytes, mesoangioblasts, and adipocytes. In some embodiments, the filter cake may contain co-cultures of fibroblast and myoblasts at a ratio of between about 95F:5M to about 5F:95M. In some embodiments, the filter cake may contain cells from a species of poultry, game, aquatic or livestock. In some embodiments the filter cake may contain cells from *Gallus gallus, Meleagris gallopavo, Anas platyrhynchos, Bos taurus, Sus scrofa, Ovis aries, Salmo salar, Thunnus thynnus, Gadus morhua, Homarus americanus, Litopenaeus setiferus, Oncorhynchus mykiss*, or *Oreochromis niloticus*.

Any suitable density of cells may be cultivated in the filter cake. In some embodiments, the initial density of cells in the unfiltered medium is between about 1-200×10$^6$ cells/ml. In some embodiments, the density of cells in the medium is between about 0.05×10$^6$ cells/ml-about 2000×10$^6$ cells/ml, about 0.5×10$^6$ cells/ml-about 200×10$^6$ cells/ml, about 5×10$^6$ cells/ml-about 20×10$^6$ cells/ml, or about 5×10$^6$ cells/ml-about 10×10$^6$ cells/ml.

In some embodiments, the filter cake is edible, meltable, and/or degradable.

Heating Element

The systems described in this disclosure may be heated. In some embodiments, the system may comprise at least one heating element. Any suitable heating element known in the art may be used. A person skilled in the art would understand how to identify and use a heating element in the systems disclosed herein. In some embodiments, the heat element may be a heat exchanger, like a tubular or plate heat exchanger. For example, the system shown in FIG. 1A contains an in-line heat exchanger 170. In some embodiments, the system may be placed in a temperature-controlled environment.

The heating element may be located at any one or more components of the system, such as the filter chamber, filter aid chambers, cell tanks, inlets, outlets, within the transfer piping etc. In some embodiments, the heating element 170 is connected to the filter chamber 110, as shown in FIG. 1A. In some embodiments, the heating element may be connected to the filter aid chambers 130 and 140. In some embodiments, the heating element may be connected to the cell tanks 150 and 160. In some embodiments, the heating element may be connected to any one or more of inlet 112, outlets 114, 116, and 118, or any other component (e.g. pipes, valves) of the system used for fluidic communication. Other methods of heating, such as jacketed tanks or temperature-controlled environments would be well known to those skilled in the art.

The heating element may maintain any suitable temperature required in the system. In some embodiments, the heating element may regulate a temperature suitable for cell cultivation. In some embodiments, the heating element may regulate the temperature of the filter chamber between about 10° C.-about 45° C. during growth. In some embodiments, the heating element may regulate a temperature of between about 37° C. In some embodiments, the heating element may regulate a temperature appropriate for sterilization, such as about 100° C. or above.

In some embodiments, the heating element may regulate a temperature appropriate for storing and/or sterilizing cell culture media, nutrient media, buffers, saline, or any other liquids.

In some embodiments, the heating element may regulate the temperature of the cells or cell biomass produced therefrom. In some embodiments, the heating element may regulate the temperature of the cell-based meat, and/or wash buffers. In some embodiments, the temperature difference between different steps (such as after pre-coat layer formation and before adding cell suspensions) of the method does not exceed a particular temperature (e.g. about 5° C.) to avoid damaging the cells. In some embodiments, before harvesting, the cell-based meat may be cooled down for further processing. In some embodiments, the cell-based meat may be heated for a certain period of time. In some embodiments, the pre-coating of the filter support with a first filter aid can be done at a high temperature to ensure sterility, before introducing cooler media to introduce cells into the process.

Media

Different types of media may be used depending on the use in the system and methods. The media described herein may have any appropriate sugar, salt, amino acids, vitamins, preservatives, buffers, osmolarity, pH value, temperature, ionic strength, viscosity, and/or ingredients (e.g. other nutrients, signaling molecules). The combination of these factors will depend on the type and application of the media, as described below. In some embodiments, the media disclosed herein may be sterile.

In some embodiments, the media is a flooding media. Flooding media may be used to add one or more filter aids on to the filter chamber to form a uniform layer of the filter aid (also referred to herein as pre-coat layer). For example, as shown in FIG. 1B the flooding media (FM) 180 may be used to add the filter aid starch 132 on to the filter supports to form the pre-coat layers 124 and 125, respectively. Examples of flooding media include sterile cell culture medium, water, and/or sterile saline. The flooding media may be heated for sterilization.

In some embodiments, the media is a filter aid media. The filter aid media may be used to suspend one or more of the filter aids. Examples of filter aid media include water, salted liquids, saline, minerals and metals, PBS, HEPES, or other media known to a person of skill in the art, to achieve, for example, the desired osmolarity, density, and functionality. For example, as shown in FIG. 1A, the filter aids 132 (starch) and 142 (cellulose) are suspended in saline as the filter aid media. Depending on the type of filter aid used, such as non-compressible starch or compressible cellulose, different filter aid media may be used. The filter aid media containing the filter aids may be heated for sterilization or cooled to prevent degradation. The filter aid media may be homogenized using an agitator, a circulation pump and/or a gas-sparger to prevent settling or floating of the filter aids. A gasification may also be implemented to prevent or force oxidation.

In some embodiments, the media is a cell culture media. The cell culture media may be used to suspend cells for cultivation. Examples of cell culture media include Eagle's Minimum Essential Media (EMEM), Dulbecco's modified Eagle's Medium (DMEM), RPMI-1640, F12 Medium, Ham's nutrient mixtures, and other nutrient media known to a person of skill in the art. In some embodiments, the media is chemically defined. In some embodiments, the media is free of animal derived serum. In some embodiments, the media is free of animal derived components.

In some embodiments, the media is a wash-out media. In some embodiments, the cell biomass is a cell-based meat. The wash out media may be used to harvest the cell-based meat and/or to impart the physical and/or organoleptic properties to the cell-based meat. Different wash out media may be used depending on the type of cell-based meat and the desired sensory and visual characteristics. For example, aqueous solutions containing red beet juice may be used for a red coloring of the cell-based meat, or other components such as iron may be added for flavor.

In some embodiments, the different media used herein have the same or similar osmolarity, to ensure that the cells do not suffer osmotic stress. In some embodiments, the filter aid media and the cell culture media containing the cells have the same or low osmotic difference. In other embodiments, the osmotic pressure might intentionally differ significantly in some parameters, to remove undesired substances out of the product by diffusion or introduce desired substances into the product, which improve the products characteristics.

In some embodiments, any of the above media may be reused after filtration. For example, the media collected through outlet (R) 190 (FIG. 1C) from the filtered chamber, may be fully or partially reused, recirculated, or enriched as required with nutrients, oxygen, buffers, signaling molecules, etc.

In some embodiments, the media may contain substances which prevent microbial growth. In other embodiments, it also includes substances specifically chosen to improve the final cell biomass's shelf life, chemical and/or physical stability, flavor, texture, color, odor, or some combination thereof.

Filter-Cake Based Methods for Cultivating Cells and Cell Biomass

Provided herein are methods for optimizing the cultivation of cells and cell biomass. In some embodiments, the method comprises, providing a filter support, adding at least one filter aid to the filter support, adding a plurality of cells to the filter aid, wherein the cells and the filter aid together comprise a filter cake, and growing the cells into a cell biomass in the filter cake, wherein the filter cake is at least partially compressible.

Providing a Filter Support

The methods disclosed herein may include providing at least one filter support. Any suitable filter support may be used, as described in the above section. Examples of filter supports include: nets, mashes, grits, cloth, sintered, porous, and perforated materials usually installed into horizontal filters, vertical filters, plate filters, plate press filters, mash filters, cloth filter or candle filters. The filter support may be of any suitable dimension. In some embodiments, the filter support has a surface area of between about 1 meter$^2$-about 500 meter$^2$. In some embodiments the filter support has a surface area of between about 1 meter$^2$-about 2000 meter$^2$.

In some embodiments, the at least one filter support may be located within a filter chamber. For example, FIG. 1A contains two filter supports 120 and 122 located within the filter chamber 110. In some embodiments, the filter support may be sterilized before being placed within the filter chamber. The filter chamber may be emptied, cleaned, and sterilized before placing the filter support. In some embodiments, the filter support and chamber are sterilized together.

Adding Filter Aids

The methods disclosed herein include adding at least one filter aid to the filter support. Any suitable filter aid may be used, as described above. Examples of filter supports include cellulose, starch, diatomaceous earth, perlites, active charcoal, vegetable fats, waxes, crystals, fibers, plant fibers, fungal mycelia, algae, naturally occurring fibers, synthetic fibers, inorganic fibers, organic fibers, husks, plant based proteins, fats, waxes, or combinations thereof. Combinations of different filter aids with different material properties such as particle sizes, functional surfaces, particle structures, and different compressibility (e.g. compressible or incompressible) may be used.

Adding the filter aid to the filter support may be carried out by any suitable method. In some embodiments, the at least one filter aid may be added by flowing media containing the at least one filter aid throughout the filter camber. The filter aid may be suspended in a fluid and added onto the filter support. For example, as shown in FIG. 1B, the filter aids starch 132 and cellulose 142, are suspended in the filter aid medium saline, and stored in filter aid chambers 130 and 140, respectively. A flooding medium, as described above, may be used to flow one or more filter aids onto the filter support.

Adding the one or more filter aids to the filter support may be carried out in any order. In some embodiments, the at least one filter aid may be added at the same time, sequentially, alternately, or in any relevant order thereto. For example, as shown in FIG. 1B, only the filter aid starch 132 is added on to the filter supports to form the pre-coating layers 124 and 125.

In some embodiments, adding the filter aid to the filter support forms a layer (also referred to herein as pre-coat layer layer) of the filter aid on the filter support. The pre-coat layer prevents high pressure build-up during filtration and prevents blockage. In some embodiments, the pre-coat layer may be uniformly distributed over the filter support.

The filter chamber may be divided into an unfiltered chamber 192, in which the media containing cells and/or filter aids is introduced, and filtered chamber 194, into which the filtered medium is discharged and optionally recirculated. For example, as shown in FIG. 1B, the pre-coat layers 124 and 125 are formed on the filter supports 120 and 122, respectively, in the unfiltered chamber 192.

In some embodiments, the filter aid is added to the filter support at between about 25 g/m$^2$-about 12000 g/m$^2$, about 50 g/m$^2$-about 6000 g/m$^2$, about 100 g/m$^2$-about 3000 g/m$^2$, about 200 g/m$^2$-about 1500 g/m$^2$, or about 400 g/m$^2$-about 750 g/m$^2$.

Adding a Plurality of Cells

The methods disclosed herein include adding a plurality of cells to the filter aid and on to the filter support. In some embodiments, a plurality of cells of the same cell type may be added. In some embodiments, a plurality of cells of different cell types may be added. The plurality of cells may be added in any relevant order (e.g. simultaneously, alternately, periodically, etc.) or time interval (e.g. hourly, daily, weekly, etc.) to create a desired structure, porosity, and or functionality within the filter cake and final product.

Any cell type may be added, as described in the above section. In some embodiments, the cells may be metazoan cells. In some embodiments, the cells are selected from the group consisting of skeletal muscle cells, stem cells, pluripotent stem cells, embryonic stem cells, induced pluripotent stem cells, fibroblasts, myoblasts, somatic cells, extraembryonic cells, myocytes, satellite cells, side population cells, muscle derived stem cells, mesenchymal stem cells, myogenic pericytes, mesoangioblasts, and adipocytes.

In some embodiments the cells exist in co-culture in the filter cake. For example, co-cultures of fibroblasts (F) and myoblasts (M) at a ratio of between about 95F:5M to about 5F:95M may be added. In another example, co-cultures of adipocytes (A) and myoblasts (M) at a ratio of between about 95A:5M to about 5A:95M may be added. In some embodiments, the cells are from a species of poultry, game, aquatic, or livestock. In some embodiments, the cells are selected from the group consisting of *Gallus gallus*, *Meleagris gallopavo*, *Anas platyrhynchos*, *Bos taurus*, *Sus scrofa*, *Ovis aries*, *Salmo salar*, *Thunnus thynnus*, *Gadus morhua*, *Homarus americanus*, *Litopenaeus setiferus*, *Oncorhynchus mykiss*, and *Oreochromis niloticus*. In some embodiments, the cells are from a plurality of a species and may be added in combination, in sequence, or some combination thereof.

Adding the plurality of cells may be carried out by any suitable method. In some embodiments, the plurality of cells is added by flowing media containing the plurality of cells. For example, as shown in FIG. 1C, myoblasts 152 and fibroblasts 162 may be suspended in DMEM cell culture media and stored or multiplied further in cell tanks 150 and 160, respectively. The cell culture media containing the fibroblast flows on to the pre-coat layers, displacing the flooding medium via outlet 190. The fibroblasts are now embedded into the pre-coat layers on the filter supports, forming the filter cakes 126 and 128 respectively.

Adding the plurality of cells may be carried out with or without addition of one or more filter aids, in any order and any time interval. In some embodiments one cell type and one filter aid may be added to the filter support simultaneously. For example, as shown in FIG. 1C, the filter aid cellulose 142 may be added along with the fibroblast 162 solution. In some embodiments, more than one cell type and more than one filter support may be added to the filter support simultaneously. For example, as shown in FIG. 1D, the filter aids cellulose 142 and starch 132 may be added along with myoblasts 152 and fibroblasts 162 to the filter supports simultaneously.

Adding the plurality of cells may be carried out in any suitable order. In some embodiments, the plurality of cells may be added at the same time, sequentially, alternately, or in any relevant order and any time interval. In some embodiments only one cell type is added. For example, as shown in FIG. 1C, only fibroblast cells 162 are added, along with the cellulose filter aid 142, to the filter supports. In some embodiments, more than one cell type is added to the filter support simultaneously. For example, as shown in FIG. 1D, both myoblasts 152 and fibroblasts 162 are added to the filter cakes 126 and 128 simultaneously.

Growing the Cells into a Cell Biomass in the Filter Cake

The methods disclosed herein include growing cells into a cell biomass in the filter cake. The filter cake comprises a plurality of cells and filter aids. In some embodiments, the filter cake is located on the filter support. In some embodiments, the filter cake is formed on a surface of the filter support facing the unfiltered chamber. For example, as shown in FIG. 1D, the filter cakes 126 and 128 are located in the unfiltered chamber 192.

Any number or density of cells may be cultured in the filter cake. In some embodiments, the initial density of cells in the media is between about 0.05×10$^6$ cells/ml-about 2000×10$^6$ cells/ml, about 0.5×10$^6$ cells/ml-about 200×10$^6$ cells/ml, about 5×10$^6$ cells/ml-about 20×10$^6$ cells/ml, or about 5×10$^6$ cells/ml-about 10×10$^6$ cells/ml.

In some embodiments, culturing the cells in the filter cake includes perfusion by media (e.g. cell culture media) containing nutrients and oxygen necessary for cell growth. As described above, the continuous perfusion of nutrient rich promotes cell-cell interaction, cross-linking, and fusion of the cells in the filter cake, enabling the assembly and formation of one or more layers of thick cell biomass.

Compressing and Decompressing the Filter Cake

In some embodiments, culturing the cells in the filter cake includes compressing the filter cake. For example, in FIG. 1E the arrows 460 show the compression and decompression of the filter cakes 126 and 128. Compressible filter aids used to create the filter cake enable changing and adapting the filter cake behavior. As discussed above, periodic compression and decompression of the filter cake enables flow of nutrient rich media and oxygen into all the layers of developing cells and tissues. The compressibility of the filter cake also enables the operator to gain information about the growth rate and adjust the porosity of the filter cake during the process. For instance, if a stable, constant circulation throughout the cell-enriched filter cake is implemented, a certain differential pressure between the unfiltered side (high pressure side) and filtered side (low pressure side), and hence a degree of filter cake compression will result. If this flow is maintained constantly the differential pressure will increase over time, as the cells grow, divide, and fuse and thereby hinder the fluid from penetrating more and more. In order to avoid clogging, the in-feed pressure and/or the flow rate can be reduced, leading to a relaxation of the cake, enabling the media to flow through the channels and pores, and compensating the degree of clogging. The pressure/flow adjustment hence can be correlated to the meat growth.

In some embodiments, the filter cake may be compressed by pressure variations. In some embodiments, the pressure between the inlet and the outlet is between about 0.1 bar-about 5.0 bar. Based on the increased pressure difference of the filtered and unfiltered chambers, and the metabolic byproducts, conclusions can be drawn about cell proliferation, cell division, and cross-linking intensity to influence the process as needed. By changing the flow rates to maintain a steady pressure difference, clogging can be avoided. Alternating the pressures will lead to compression and decompression of the filter, allowing channels to form and supplying the cells in deeper layers with nutrient and oxygen enriched media.

In some embodiments, the filter cake may be compressed by flow rate and/or flow direction variations. In some embodiments, the flow rate between the inlet and the outlet is between about 1 L/min-about 1000 L/min. In some embodiments, the flow may be from top to bottom of the filter chamber, from bottom to top of the filter chamber, from both sides, and/or in crossflow mode. For example, as shown in FIG. 1B, the flow may enter the filter chamber from inlet 112 and exit via outlets 114 and 116. The flow rates and/or the flow directions may be varied periodically.

Culturing may be carried out at temperature ranges suitable for cell growth, such as between about 10° C. to about 45° C. during growth. As discussed above, temperature-controlled environments or heating elements, such as the heat exchanger 170 may be used to set a suitable temperature, such as about 37° C. In some embodiments, the product is cooled below 10° C. before filtration by actively cooling it and/or using cold wash buffers.

Harvesting

In some embodiments, the method may include harvesting the cultivated cells or the cell biomass produced therefrom, from the filter cake. After the cell biomass produced from the cultivated cells has reached a desired state (e.g. degree of growth, cell divisions, cross-linking, fiber formations, protein content, and/or overall mass), a complete or partial degradation of filter aids can optionally be induced in the filter chamber itself, for example by adding enzymes (which, for example, degrade starch and/or cellulose), adding acids or bases, and/or implementing temperature embodiments. In some embodiments, the tissue may be obtained by physical methods (e.g. centrifugation, gravity-assisted settling), chemical methods, enzymatic methods, sedimentation, concentration, flocculation, and the like.

In some embodiments, the method may include harvesting the cultivated cells and/or the cell biomass produced therefrom, from the filter cake, without the need to degrade or otherwise remove the filter aid. For example, filter cakes comprising one or more edible filter aids, thus obviating additional steps to remove or degrade filter aids. In some embodiments, the filter cake is edible. In other embodiments, the filter cake may comprise filter aids that are edible by the cell or degraded by the cell's secretions, whereby the filter aids are consumed, degraded, or both as the cell biomass grows.

In some embodiments, a washing medium may be used alternatively or additionally and, if necessary, circulated for a certain period of time in order to influence the organoleptic properties (sensory and visual) of the cell biomass. For example, the washing medium may be a slightly salty aqueous solution or a washing solution with a coloring effect (e.g. by adding juice from red beet).

In some embodiments, harvesting is carried out under sterile conditions. In some embodiments, the product is cooled down prior to harvest. The filter may be emptied and blown through with gas (air) to dry the product. In some embodiments, such as press filters, a pressing step (e.g. membrane compression) can be implemented during the process, to de-wett the filter cake, and/or to the product.

Methods for Establishing Perfusion Through a Growing Cell Biomass

Provided herein are methods for establishing perfusion through a growing cell biomass. In some embodiments, the method comprises seeding cells on an at least partially compressible filter aid, compressing the cells, the at least partially compressible filter aid, or both, flowing media through the at least partially compressible filter aid to grow the cells into a cell biomass, whereby growth reduces perfusion over time, decompressing the cells, the at least partially compressible filter aid, or both, to increase perfusion of media.

In some embodiments, the cell biomass is compressed by a fluid pressure or flow of the media. In some embodiments, the cell culture media provides nutrients and oxygenation to promote cell growth. In some embodiments, the cell biomass is decompressed with a relief valve, a lower pressure media flow, flow reduction of the media, or some combination thereof. In some embodiments, the cell biomass, its substrate, or both are decompressed proportionally to the growth of the cell mass, whereby perfusion is stabilized. In some embodiments, the cell biomass, the at least partially compressible filter aid, or both cycle between a compressed state and a decompressed state at a pulsing frequency.

In some embodiments, the pulsing frequency is about 1 second, about 10 seconds, about 30 seconds, about 50 seconds, about 1 minute, about 2 minutes, about 4 minutes, about 6 minutes, about 8 minutes, about 10 minutes, about 12 minutes, about 14 minutes, about 16 minutes, about 18 minutes, about 20 minutes, about 30 minutes, about 60 minutes, about 2 hours, about 4 hours, about 8 hours, about 16 hours, about 24 hours, or about 48 hours. In some embodiments, the pulsing frequency is between about 1 second and about 48 hours. In some embodiments, the pulsing frequency is between about 20 seconds and about 20 minutes.

Provided herein is another exemplary filter cake-based system 200 (FIG. 2A) for cultivating cells and cell biomass, and methods thereof.

Figure 2A:
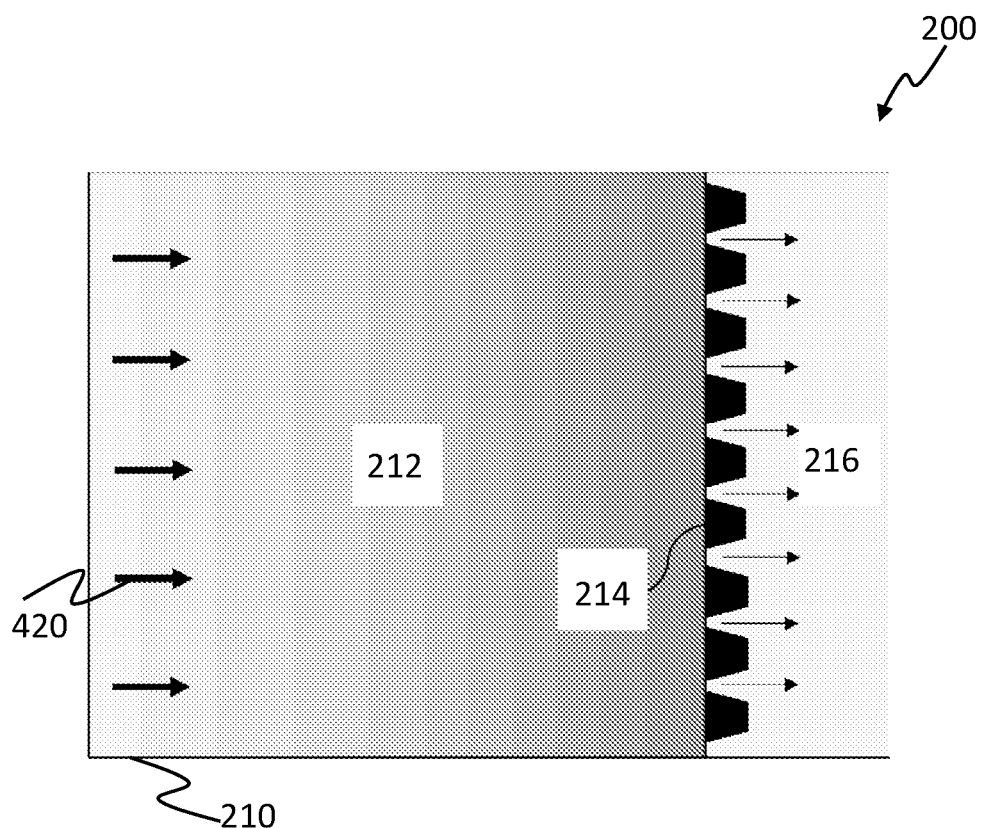
FIGS. 2A-2N depict another exemplary system and method of the disclosure for cultivating cells and cell biomass.

FIG. 2A shows a zoomed in section of a filter chamber 210, a filter support 214 (e.g. a filter-candle, a filter-mash, a filter-cloth, or a filter-sieve), with the unfiltered chamber 212 on the left side of the filter support 214, and the filtered chamber 216 on the right side of the filter support 214. The main flow direction here is from left to right, shown by black arrows 420 in FIG. 2A. The unfiltered chamber 212 will typically have a higher pressure, because the surface and pores of the filter support will block and restrict flow, which will lead to pressure losses. This difference in pressure is increased when the filter support contains small or fine pores.

Figure 2B:
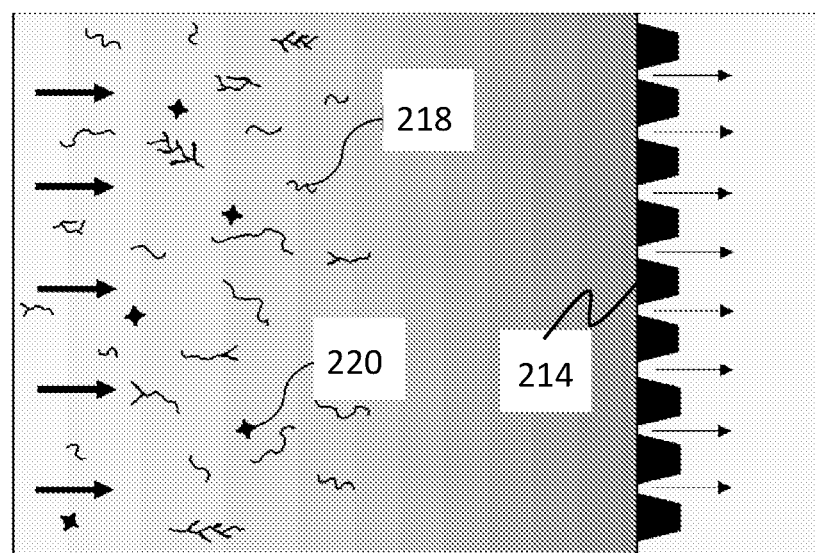

In some embodiments, the filter support 214 is flooded and sterilized, and the pre-coating step is carried out. FIG. 2B illustrates the introduction of pre-coating agents, such as filter aids into the fluid stream. In this example, pre-coating agents such as compressible filter aids 218 (such as fungi fibers or cellulose) and a small increment of incompressible filter aids 220 (such as native starch kernels) are introduced into the fluid stream, wherein they flow towards the filter support 214. In one example, a combination of about 90% to about 95% compressible filter aids and about 10% to about 5% incompressible filter aids provides a favorable compressibility profile. In some embodiments, the median particle size of the pre-coating filter aids are larger than later added filter aids to enable optimal filtration.

Figure 2C:
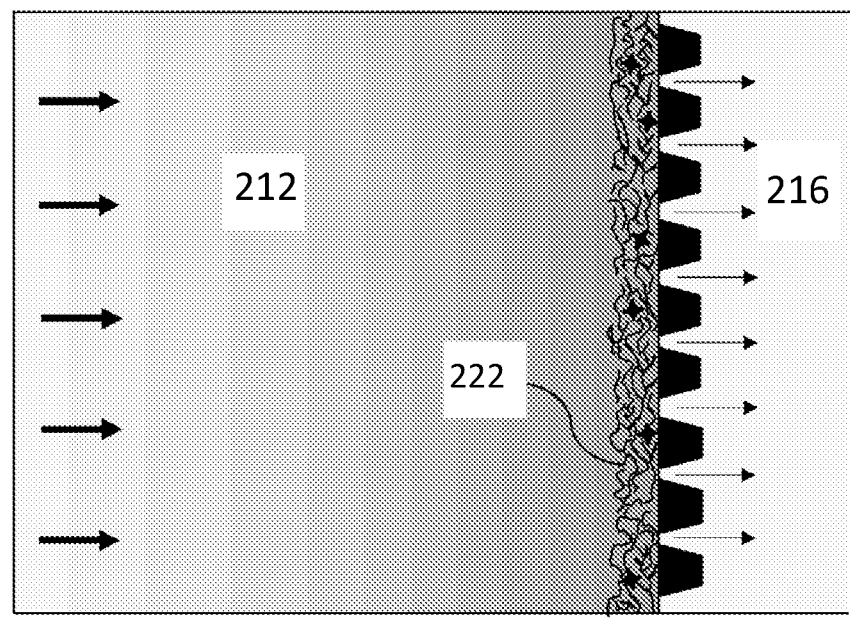

FIG. 2C shows the pre-coat layer 222. Its degree of compression and hence the porosity of the filter cake are dependent on the materials used and the differential pressure between unfiltered chamber 212 and filtered chamber 216 (flow speed dependent). Faster flows lead to a higher degree of compression and a higher difference between the unfiltered chamber and filtered chamber. For instance, finer particles and a higher-pressure differential both lead to a more compressed and less porous filter cake, while large particles and a lower pressure differential lead to a more relaxed (or decompressed) and more porous filter cake.

Figure 2D:
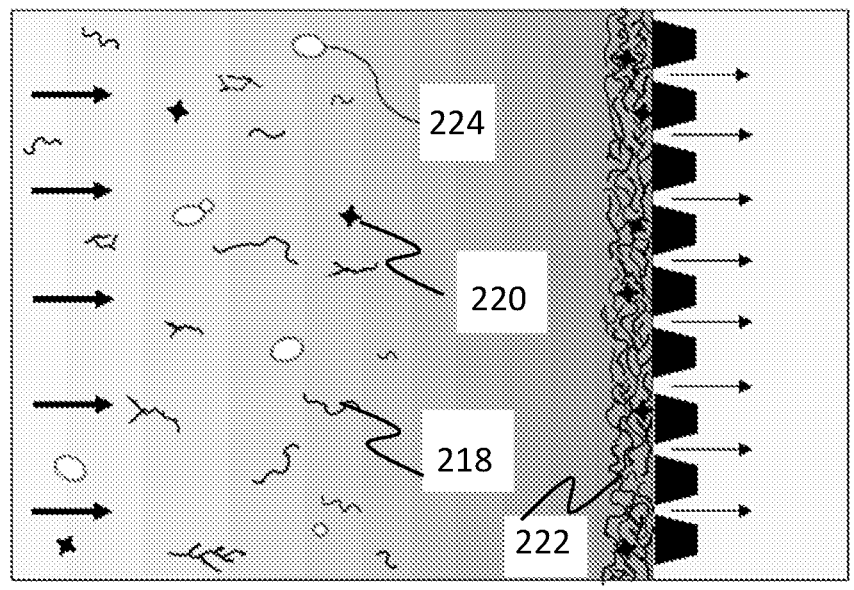

FIG. 2D illustrates the introduction of a first cell type 224 into the fluid stream (such as the various exemplary media described above), which also contains filter aids 218 and 220, and optionally other finer filter aid compositions. The fluid stream directs the first cell type 224 and the additional filter aids towards the pre-coat layer 222.

Figure 2E:
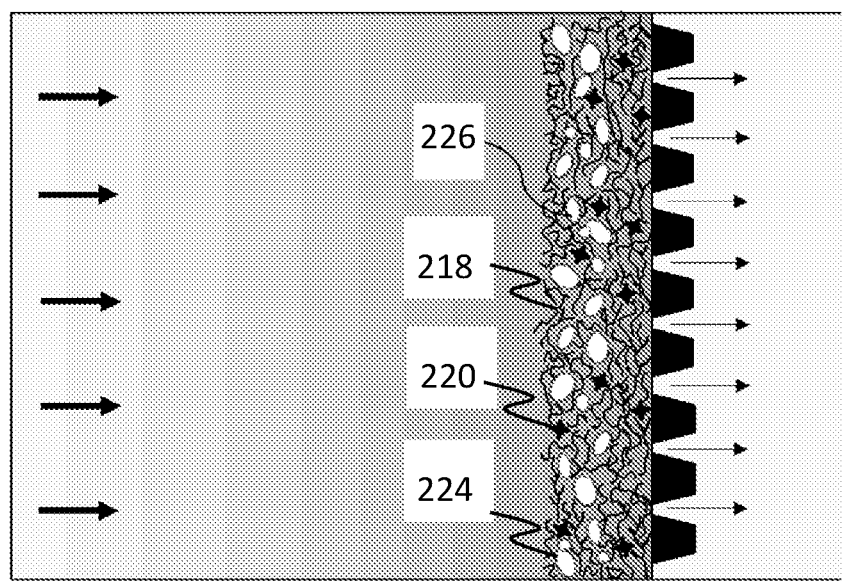

FIG. 2E illustrates the first cell type 224 embedded between both compressible particles 218 and incompressible particles 220, to form a first layer of the filter cake 226. In this example, the first cell type 224 is partially embedded in the filter aids of the initial filter cake and fully embedded within the filter aids that were flowed simultaneously with the first cells. In one example, cells are seeded in a combination of about 90% to about 95% compressible filter aids and about 10% to about 5% incompressible filter aids.

Figure 2F:
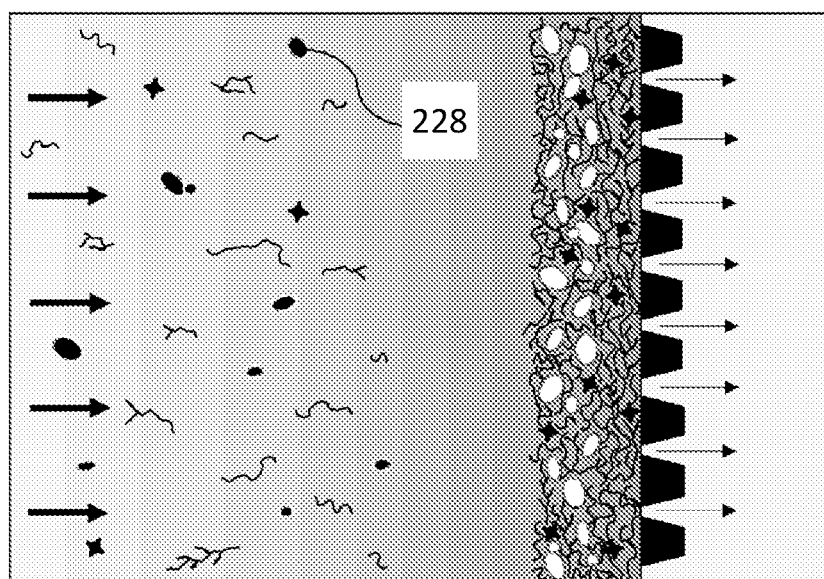

FIG. 2F illustrates an example where a second cell type 228, along with additional filter aids, is introduced into the fluid to create an additional functional layer. Alternatively, co-cultures or single cell types may be used. Although the figures illustrate pauses between each of the individual dosing steps, in some embodiments, these processes may be done continuously. In some embodiments, a constant differential pressure between unfiltered chamber and filtered chamber is maintained during this process to ensure a constant homogeneous porosity of the cake. Since the filter cake resistance increases with increasing thickness, the flow speed (and hence amount) typically must be reduced to maintain the desired constant differential pressure.

Figure 2G:
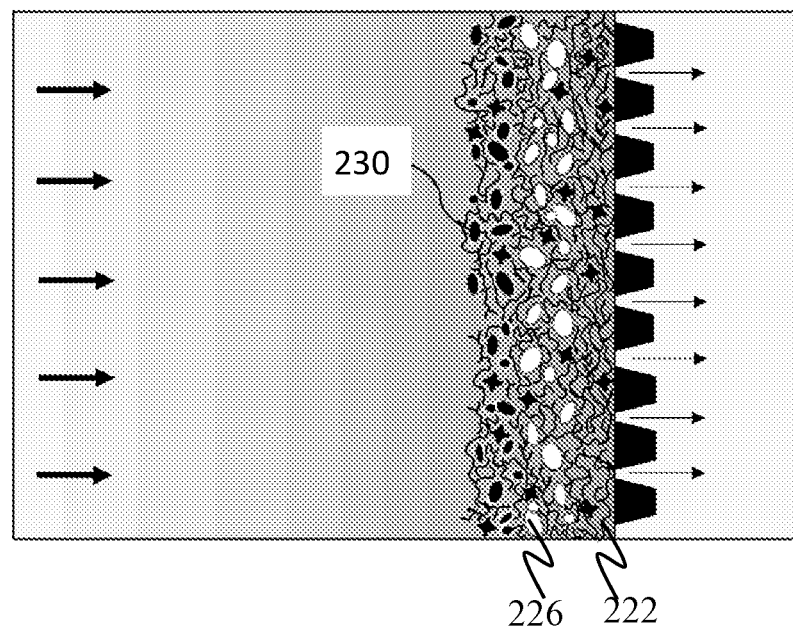

FIG. 2G illustrates the second cell type, along with its filter aids, forming a second layer 230 of the filter cake. The second cell type may be comprised of any cell type as disclosed herein, (such as muscular cells, fat cells, skeletal cells, or structural cells) which can be alternated and/or mixed in any order as desired. In this example, the filter cake is comprised of a bottom layer of only filter aids (222), a middle layer (226) of a first type of cell mixed with filter aids, and a top layer of a second type of cell mixed with filter aids (230). As the filter cake is thickened and the cells grow, pressure may build in the unfiltered chamber, which may lead to a compression of the filter cake, a reduction in porosity, and a reduction in flow through the filter cake.

Figure 2H:
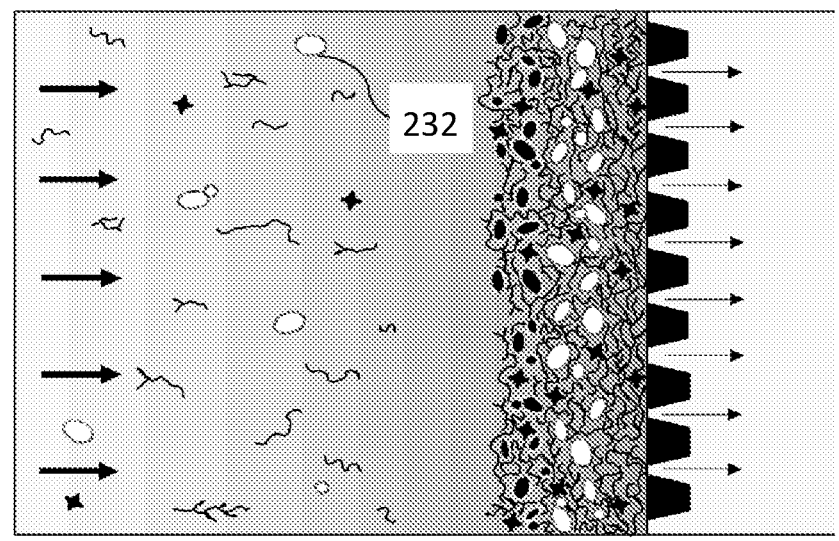

FIG. 2H illustrates the addition of a third cell type 232 along with filter aids into the fluid, wherein they are directed towards the filter cake.

Figure 2I:
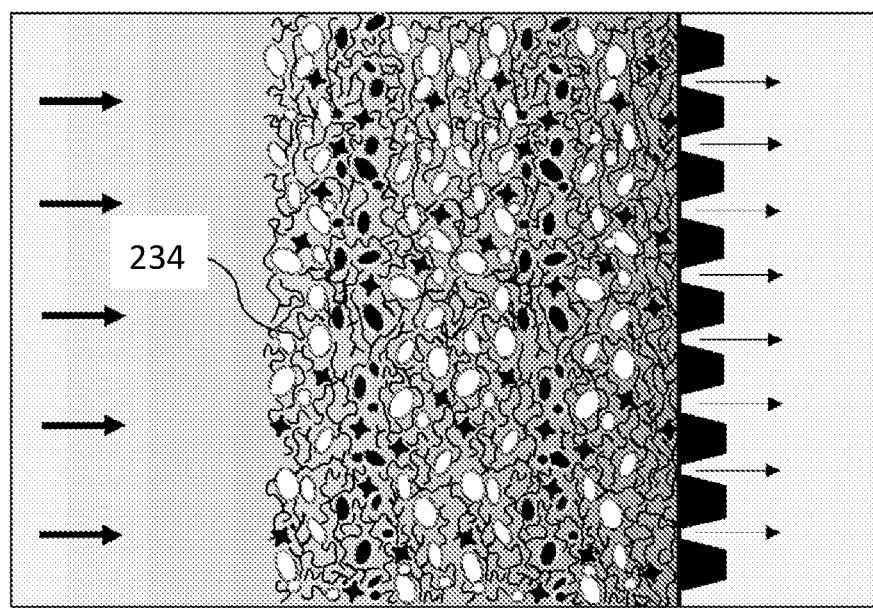

FIG. 2I illustrates a filter cake 234 layered with cells and filter aids many times over. This process can be repeated until the unfiltered chamber is filled to a high degree. Besides the number of cells, the amount and type of filter aids which are dosed into the stream, and the flow speed can be varied in any of the methods herein.

Figure 2J:
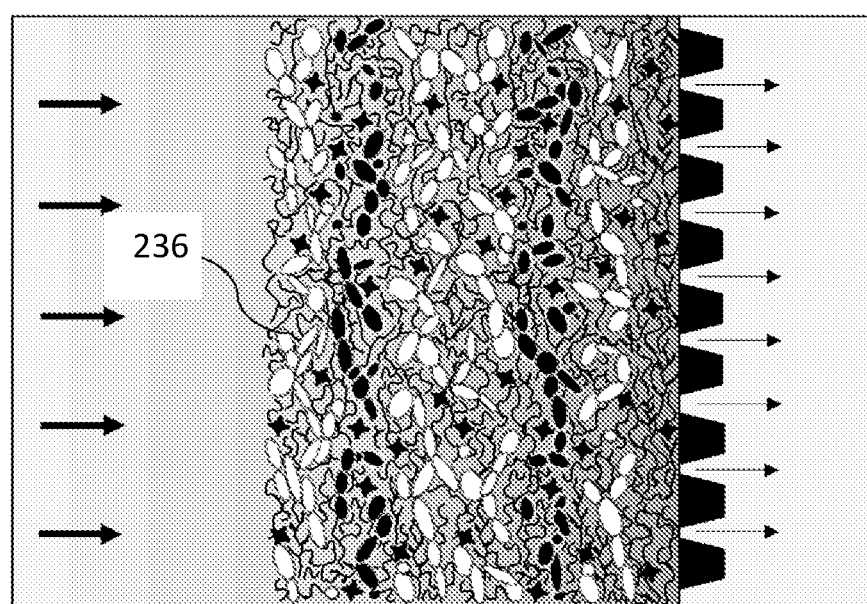

After the dosage of cells and filter aids is completed, nutrient and oxygen enriched cell culture medium is flown through the filter cake to promote cell growth and fusion of cells into cell biomass 236 (FIG. 2J).

Figure 2K:
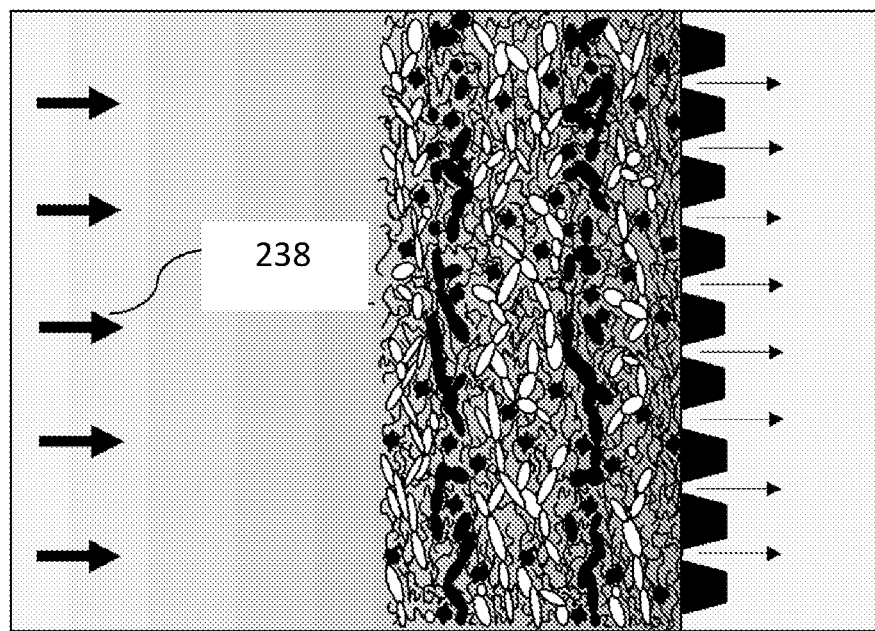

FIG. 2K illustrates an example of a filter cake compressed by high flow 238 (thick arrows). High flow leads to more cell-cell-contact and enables efficient cell fusion and tissue formation. Additionally, the active compression caused by the onset of high flow forces cells, cell culture media, and oxygen to penetrate deeply into the filter cake. On the other hand, static compression may be associated with a decrease in porosity, whereby perfusion of culture media and oxygen becomes restricted, which may increase the risk of cell death if prolonged. This can be followed by one or multiple compression phases to supply the cells closer to the filter support with oxygen and nutrient enriched medium and remove undesired components. The cell biomass thickness, robustness and cell biomass will increase during these processes.

Figure 2L:
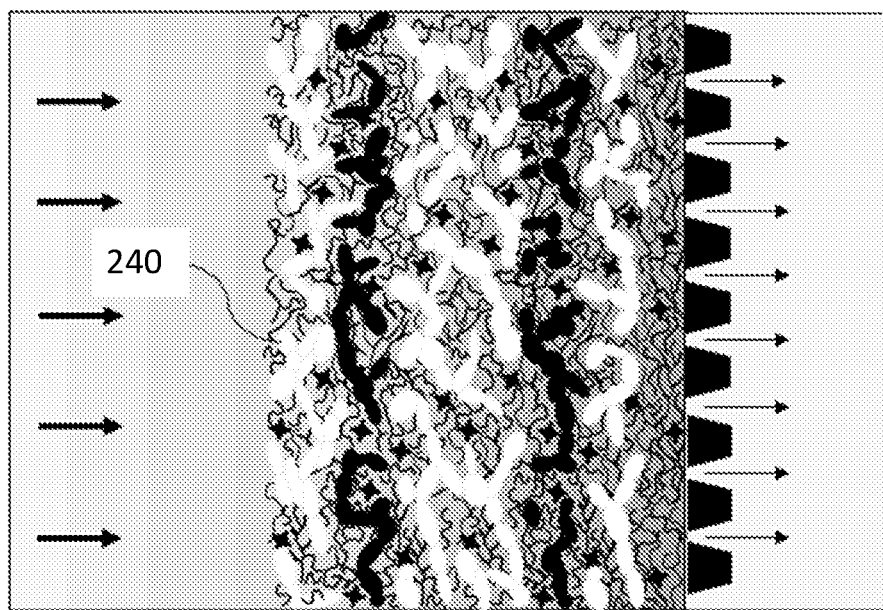

FIG. 2L illustrates an example of a filter cake 240 decompressed by low flow, e.g. a relaxation phase. In this example, the compressed filter cake initially under high flow is subsequently exposed to a low flow to generate a decompressed filter cake 240. In such instances, the transition of the filter cake from a compressed state to a decompressed state may provide several advantages to the cells within the filter cake. As the filter cake actively expands into a decompressed state, pores open throughout the filter cake and fresh cell culture media is pulled deeply and rapidly into the filter cake. A static low pressure system may maintain the shape and size of the pores, at least temporarily, formed during the decompression process, and thereby may establish stable perfusion to cells deep within the filter cake. However, as the cells grow and expand, the pores may become occluded, thereby necessitating another compression and decompression cycle. The biomass and degree of growth and fusion of the cell biomass may be determined by analyzing the biomass consumption rates, the decrease of flow speed if a constant differential pressure is maintained, and/or the increase of pressure difference during a constant flow.

Figure 2M:
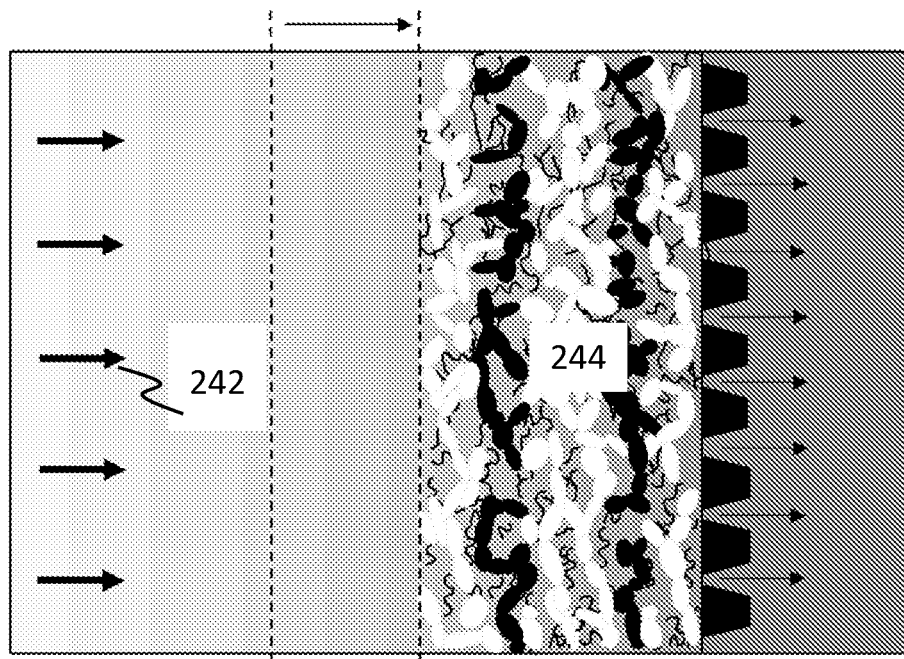

Once the desired biomass and degree of growth/fusion is achieved, the grown cell biomass may be washed. In the context of biomass production for the generation of a cell-based meat product or other applications where relevant, the washing step may adjust flavor, color and other organoleptic, chemical, or physical properties. FIG. 2M illustrates an additional, optional step, where fluids 242 are added to degrade parts of the filter aid and enrich the cells per cake volume 244. Degradation and enrichment of the filter aid may be achieved with enzyme enriched and/or tempered fluid compositions.

Figure 2N:
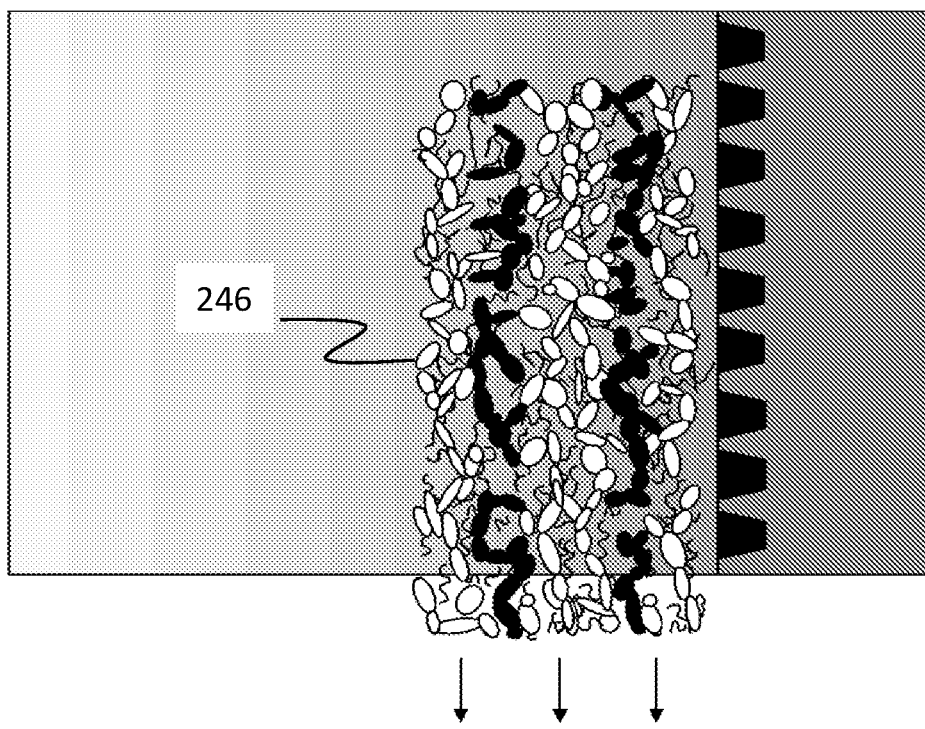

As shown in FIG. 2N, by stopping or reducing the flow speed or displacing the fluid with gas enables harvest of the cell biomass product 246. FIG. 2N illustrates the harvest of a grown cell mass. In this example, the grown cell biomass is harvested by reducing the flow speed, thereby removing the pressure holding the grown cell biomass against the filter support and allowing gravity to overcome friction resulting in the cell biomass falling off. Alternatively, the grown cell biomass may be collected by displacing the flow of fluid with a flow of gas, which causes the grown cell biomass to fall off.

Provided herein is yet another exemplary filter cake-based system 300 (FIG. 3A) for cultivating cells and cell biomass, and methods thereof. FIGS. 3A-3M illustrate an alternative filtration approach comprising a double-sided, vertical, and membrane press filter. This enables the option to change flow and compression directions, which enables obtainment of thicker filter cakes and/or lower moisture content in the cell biomass product.

Figure 3A:
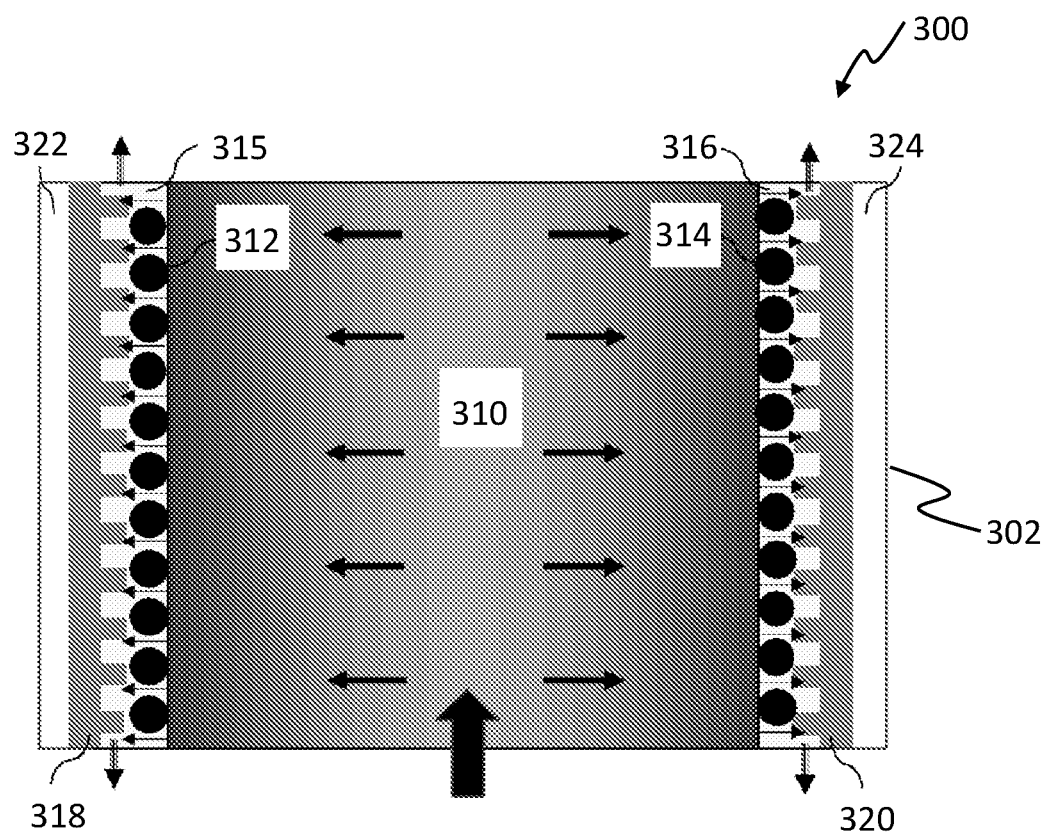
FIGS. 3A-3M depict yet another exemplary system and method of the disclosure for cultivating cells and cell biomass.

FIG. 3A illustrates an exemplary system 300 comprising a filter chamber 302, containing an unfiltered chamber 310, two filter supports 312 and 314 (such as filter cloth), two filtered chambers 315 and 316, two flexible structured membranes 318 and 320, and two membrane-blow-up chambers 322 and 324. The two membrane blow-up chambers 322 and 324 can be used to inflate the membranes and reduce the unfiltered chamber volume.

Figure 3B:
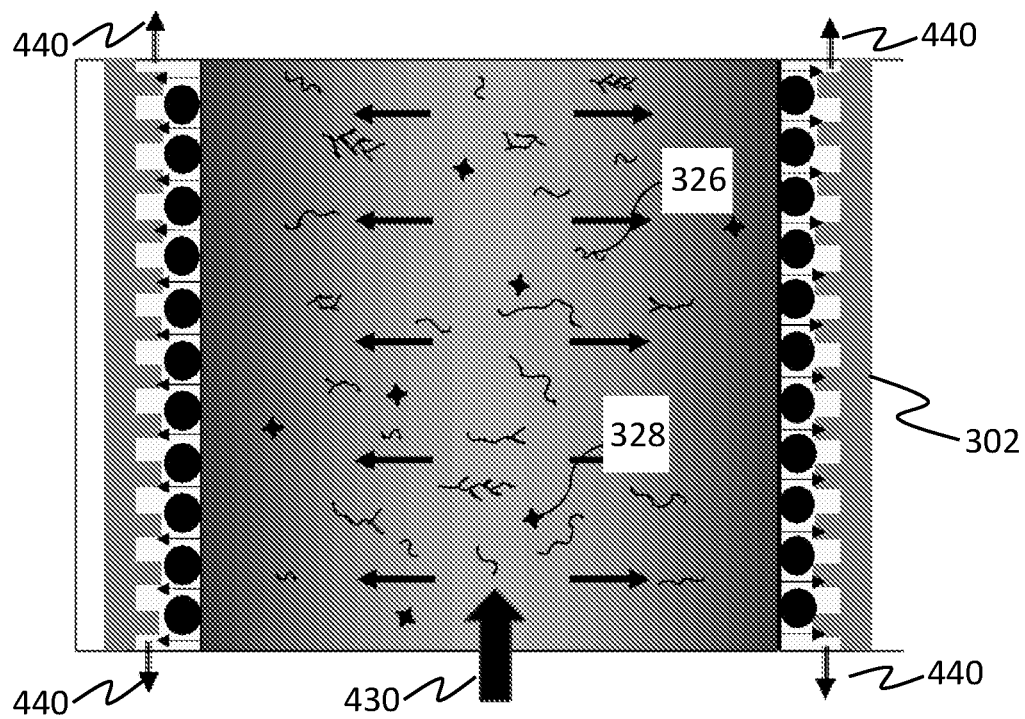

As shown in FIG. 3B, after cleaning, sterilization, and flooding, a fluid containing fibrous compressible filter aid 326 and a small increment of a less compressible filter aid 328 is introduced (indicated by the central thick arrow 430) into the unfiltered chamber to form the pre-coat. The filtered fluid exits the filter chamber, behind the filter supports, from the filtered chambers (indicated by the thin arrows 440 at the top and bottom corners to the right and left side of the filter chamber 302).

Figure 3C:
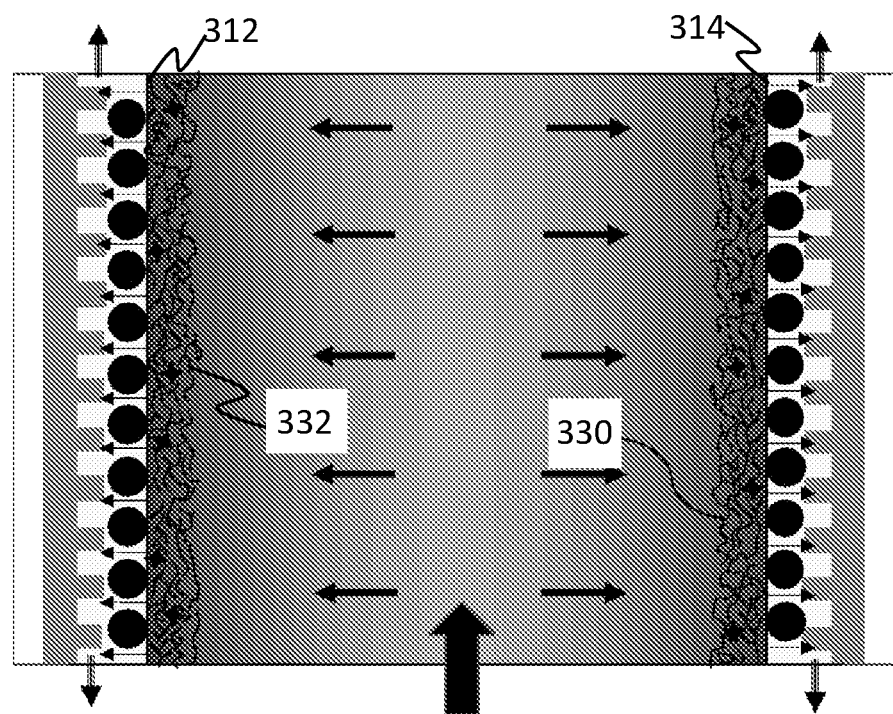
Figure 3D:
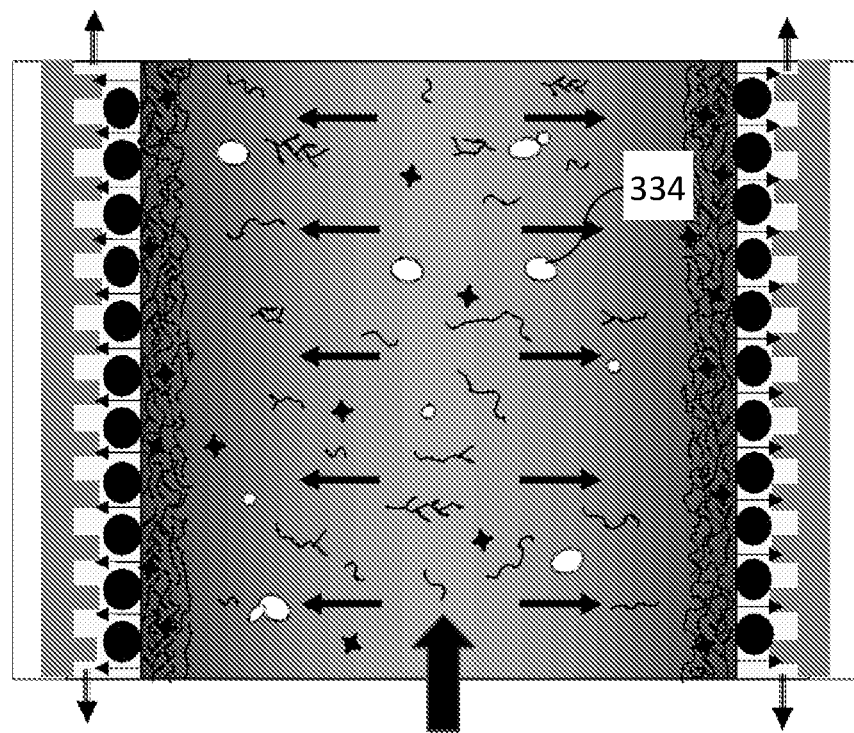
Figure 3E:
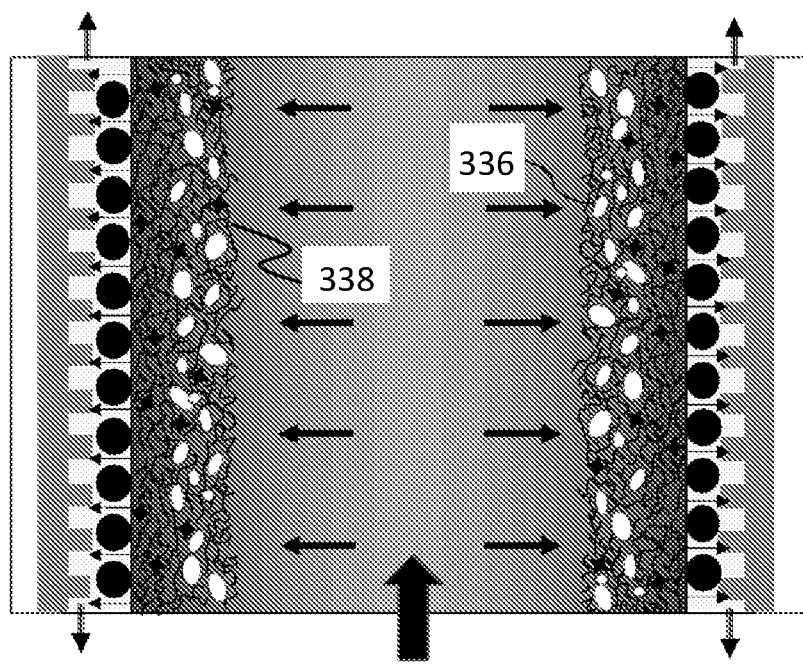
Figure 3F:
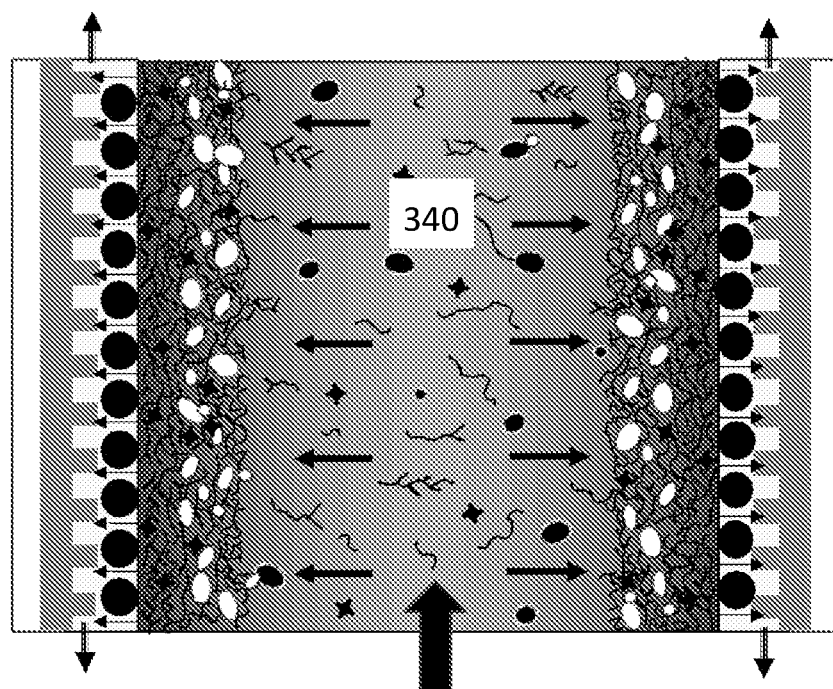
Figure 3G:
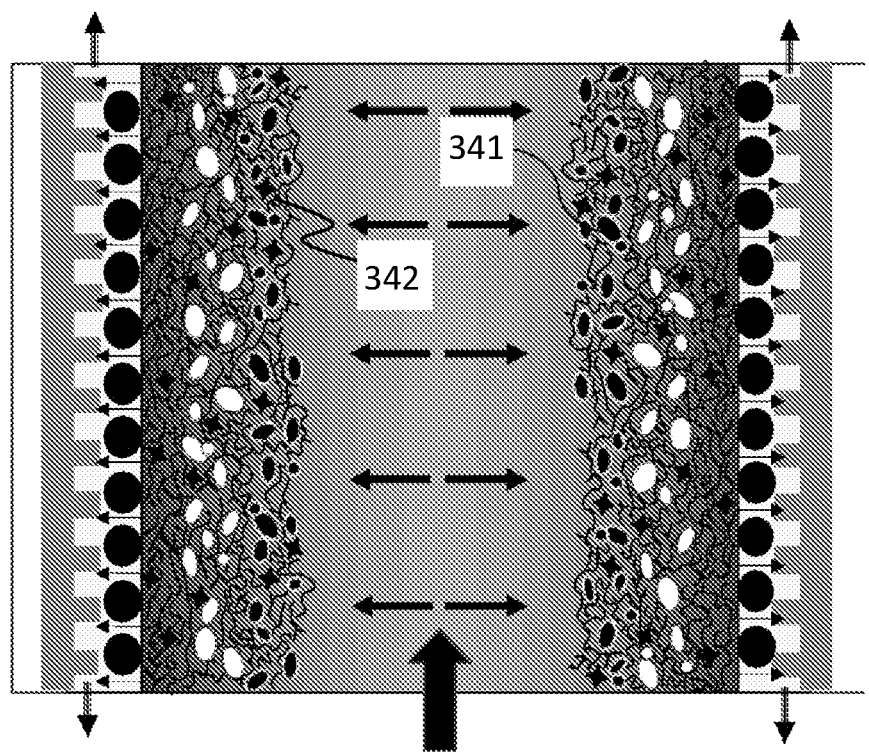
Figure 3H:
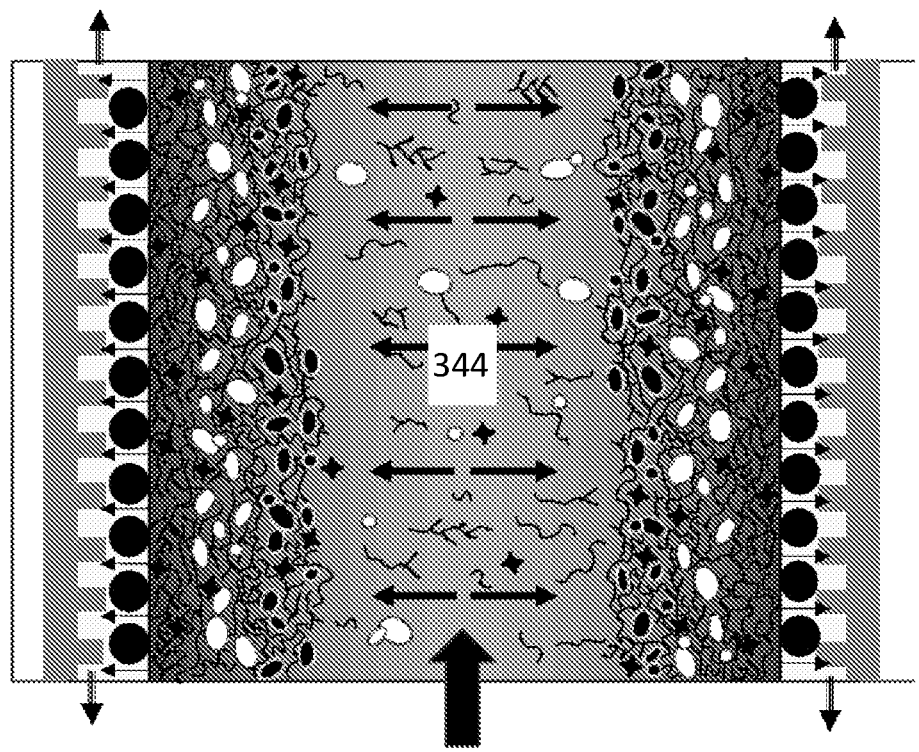
Figure 3I:
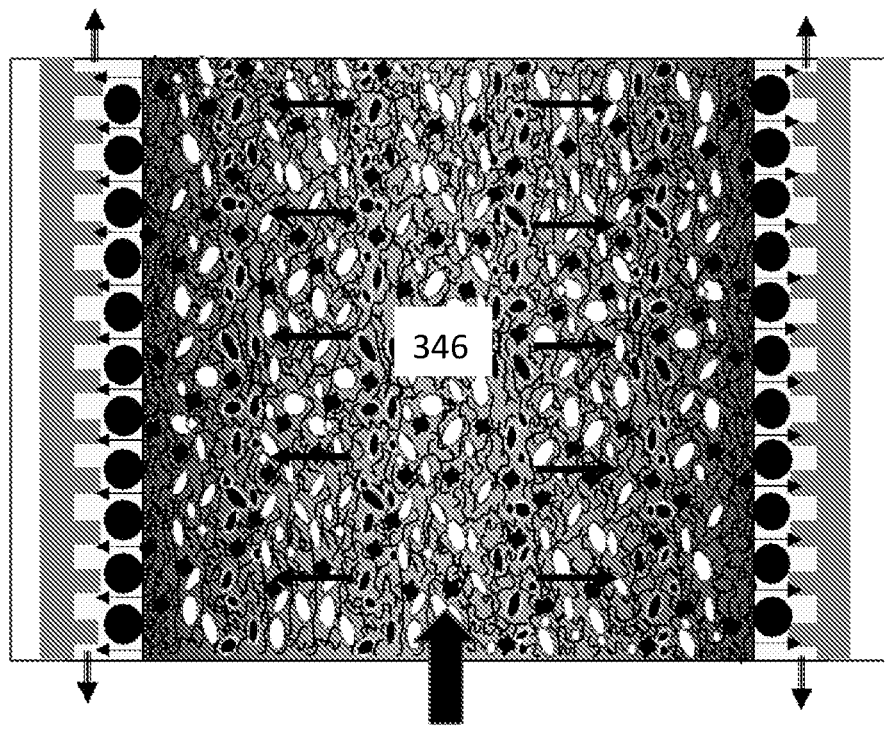

FIG. 3C shows the pre-coat layers 330 and 332 covering both the filter supports 314 and 312, respectively. Next, a first cell type 334 is subsequently added into the fluid stream, along with edible filter aids (FIG. 3D). As shown in FIG. 3E, the cells are embedded into the filter aids, forming the first layer of filter cakes 336 and 338 respectively. Next, a second cell type 340 is added, as shown in FIG. 3F. This results in additional layers being added to the filter cakes 341 and 342 (FIG. 3G). Further, as shown in FIG. 3H the addition of other cell types 344 can be repeated and/or alternated as desired. The process can be repeated until the unfiltered chamber is fully filled, for example 346 in FIG. 3I, whereby the two initial filter cakes of the unfiltered chamber are merged into a single, thicker filter cake.

Figure 3J:
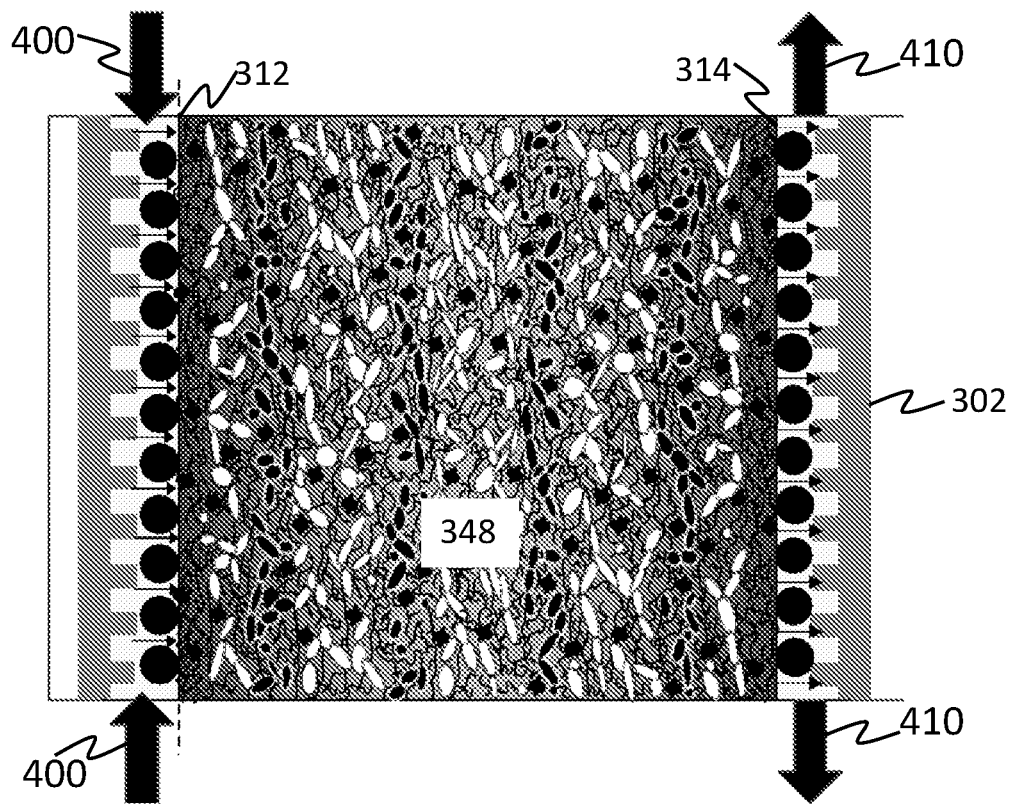

After the unfiltered chamber is filled, the flow direction can be changed (FIG. 3J). As a result, the nutrient and oxygen enriched media is introduced from behind the left filter support 312 (shown by arrows 400 at the top and bottom of the left side of the filtered chamber 302). The fluid penetrates the porous cell biomass 348 and exits on the right filter support 314 (shown by arrows 410 at the top and bottom of the right side of the filtered chamber 302). Because a thick layer can lead to starvation or intoxication of cells further away from the supply, this flow direction can be alternated, and the media can also flow from right to left. This design hence enables the creation of thicker filter cakes (e.g. essentially twice as thick) in which cells grow, multiply, fuse, and form thick cell biomass.

Figure 3K:
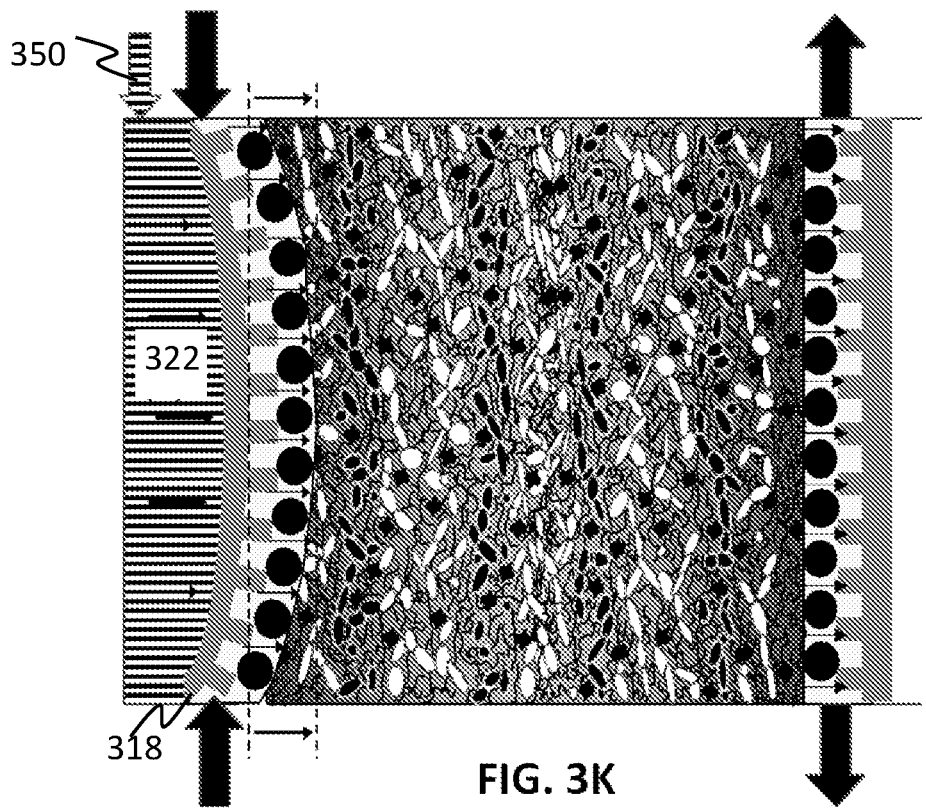

In some embodiments, to impact the porosity and cell-cell-contact, one or both membranes can be inflated or deflated, as shown in FIG. 3K. Inflating the membrane blow-up chamber 322 may be achieved by using gas and/or liquid 350. Manipulating the unfiltered chamber volume (periodically or just once) can be beneficial during pre-coating, filling, cell growth, and or discharge. It helps, for instance, to pulsate fluid in deep layers of the filter cake and may help open flow paths for fluid that were otherwise closed by the growth of the growing cell mass. The inflation and deflation side can thereby be varied. In the example shown by FIG. 3K, the compression of the left side is augmented by flow from the left side, whereby the compression helps the flow penetrate deeper into the filter cake.

Figure 3L:
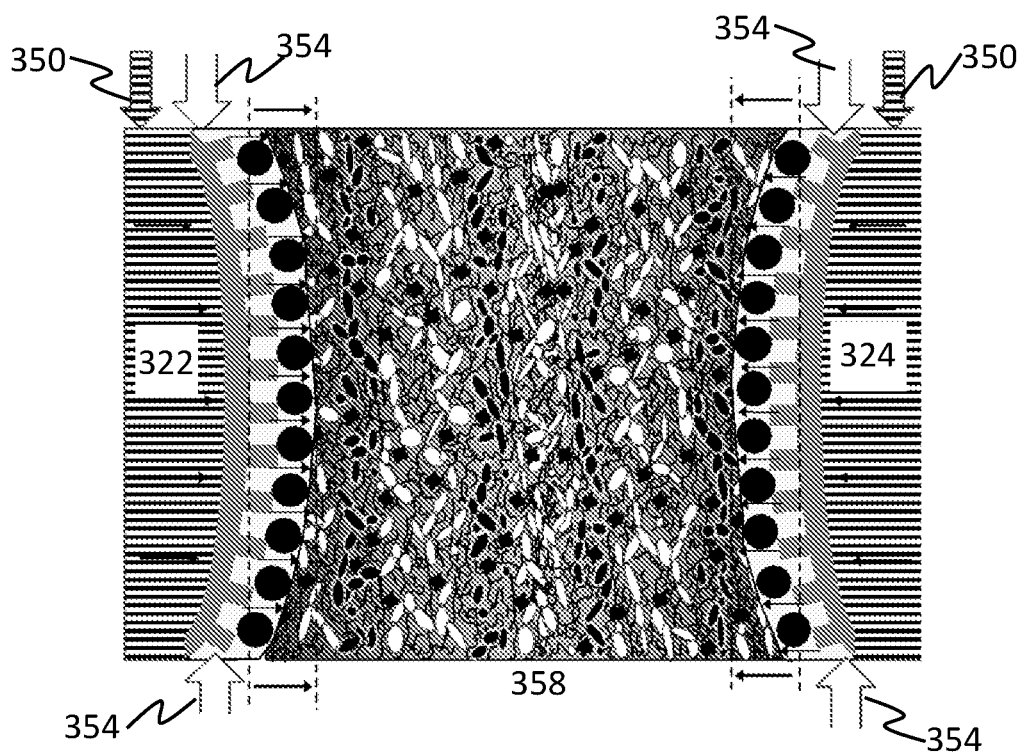
Figure 3M:
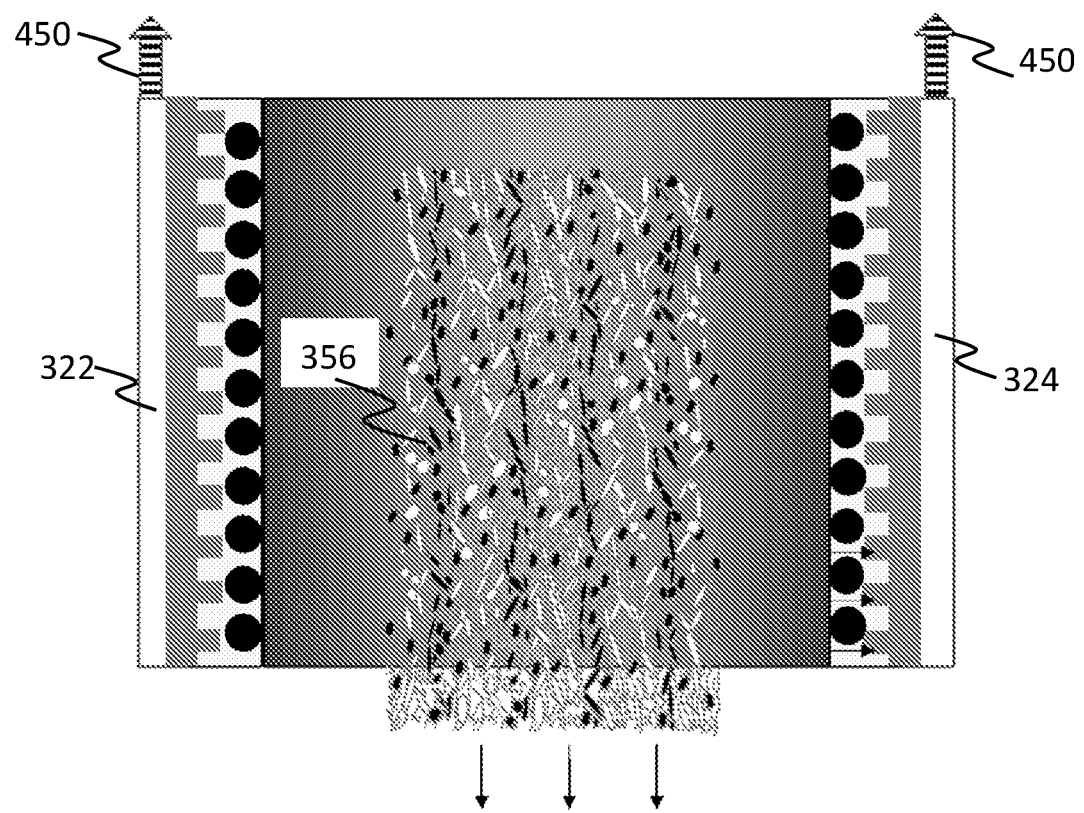

The membrane and blow up chamber enable the filter cake to be compressed before it is emptied, for instance, to reduce the final moisture content of the cell biomass product. FIG. 3L shows that both membrane blow-up chambers 322 and 324 are inflated, and a gas 354 is introduced to compress and de-wet the filter cake. The fluid is discharged via the filter inlet 358, or alternatively via one of the filter chambers sides. Subsequently, as shown in FIG. 3M, the blow-up chambers are deflated (indicated by arrows 450), so that the filter cake 356 can fall off and be harvested when the unfiltered chamber is opened.

Applications

The systems and methods described herein may be used to cultivate cells and/or cell biomass therefrom for a variety of applications. In some embodiments, the cells and/or cell biomass are cultivated into meat products intended for human or non-human consumption. In some embodiments, the cells and/or cell biomass are cultivated into cell-based meat (also known as in vitro produced cell-based meat, cell culture-based meat, in vitro meat, cultured meat, lab-grown meat, or clean meat).

In some embodiments, the cells are cultivated into a tissue intended for therapeutic purposes. Examples of therapeutic use include cultivation of stem cells, hepatocytes, 3D cell culture, cell spheroids, nodules, organoids, bio-fabrication, bio-engineering, and the like.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and embodiments are possible in view of the above teachings. The embodiments were chosen and described in order to explain the principles of the invention and its practical applications. These thereby enable others skilled in the art to utilize the invention and various embodiments with various modifications as are suited to the particular use contemplated. It is intended that the following claims and their equivalents define the scope of the invention.

Exemplary Embodiments

Some embodiments of this disclosure relate to Embodiment I, as follows:

Embodiment I-1. A method for cultivating cells and cell biomass, the method comprising:
　a) providing a filter support;
　b) adding at least one filter aid to the filter support;
　c) adding a plurality of cells to the filter aid, wherein the cells and the filter aid together comprise a filter cake; and
　d) culturing the cells in the filter cake, wherein the filter cake is perfused with media.

Embodiment I-2. The method as in embodiment I-1, wherein the filter support is selected from the group consisting of a horizontal filter, vertical filter, plate filter, plate press filter, mash filter, cloth filter, and candle filter.

Embodiment I-3. The method as in any one of embodiments I-1 to I-3, wherein the filter aid is selected from the group consisting of cellulose, starch, diatomaceous earth, perlites, active charcoal, plant fibers, fungal mycelia, algae, and organic fiber.

Embodiment I-4. The method of embodiment I-3, wherein the organic fiber comprises a length of between about 1 μm-20 μm, 20 μm-50 μm, 50 μm-80 μm, 80 μm-110 μm, 110 μm-140 μm, 140 μm-170 μm, 170 μm-200 μm, 200 μm-230 μm, 230 μm-260 μm, 260 μm-290 μm, or 290 μm-320 μM.

Embodiment I-5. The method of embodiment I-3, wherein the organic fiber has a fiver titer of between about 0.01 dtex-120 dtex, 0.05 dtex-60 dtex, 0.1 dtex-30 dtex, 0.2 dtex-15 dtex, or 0.5 dtex-5 dtex.

Embodiment I-6. The method as in any one of embodiments I-1 to I-5, wherein the filter aid is compressible.

Embodiment I-7. The method as in any one of embodiments I-1 to I-6, wherein the filter aid is compressible by between about 70%-75%, 75%-80%, 80%-85%, 85%-90%, 90%-95%, 95%-98%, or 98%-100%.

Embodiment I-8. The method as in any one of embodiments I-1 to I-7, wherein the filter aid is hollow.

Embodiment I-9. The method as in any one of embodiments I-1 to I-8, wherein the filter aid is edible.

Embodiment I-10. The method as in any one of embodiments I-1 to I-9, wherein the filter aid is degradable.

Embodiment I-11. The method as in any one of embodiments I-1 to I-10, further comprising compressing the filter cake by varying the flow rate of the media.

Embodiment I-12. The method as in any one of embodiments I-1 to I-11, further comprising compressing the filter cake by varying the pressure.

Embodiment I-13. The method as in any one of embodiments I-1 to I-12, wherein the filter aid is added to the filter support at between about 25 g/m 2-12000 g/m 2, 50 g/m 2-6000 g/m 2, 100 g/m 2-3000 g/m 2, 200 g/m 2-1500 g/m 2, or 400 g/m 2-750 g/m$^2$.

Embodiment I-14. The method as in any one of embodiments I-1 to I-13, wherein the density of cells in the filter cake is between about $0.05 \times 10^6$ cells/ml-$2000 \times 10^6$ cells/ml, $0.5 \times 10^6$ cells/ml-$200 \times 10^6$ cells/ml, $5 \times 10^6$ cells/ml-$20 \times 10^6$ cells/ml, or $5 \times 10^6$ cells/ml-$10 \times 10^6$ cells/ml.

Embodiment I-15. The method as in any one of embodiments I-1 to I-14, wherein the temperature is maintained at between about 10° C.-about 45° C.

Embodiment I-16. The method as in any one of embodiments I-1 to I-15, wherein the cells are metazoan cells.

Embodiment I-17. The method as in any one of embodiments I-1 to I-16, wherein the cells are selected from the group consisting of skeletal muscle cells, stem cells, pluripotent stem cells, embryonic stem cells, induced pluripotent stem cells, fibroblasts, myoblasts, somatic cells, extraembryonic cells, myocytes, satellite cells, side population cells, muscle derived stem cells, mesenchymal stem cells, myogenic pericytes, mesoangioblasts, and adipocytes.

Embodiment I-18. The method as in any one of embodiments I-1 to I-17, wherein the cells are co-cultures of fibroblast and myoblasts at a ratio of between about 95F:5M to 5F:95M.

Embodiment I-19. The method as in any one of embodiments I-1 to I-18, wherein the cells are from a species of poultry, game, aquatic, or livestock.

Embodiment I-20. The method as in any one of embodiments I-1 to I-19 wherein the cells are selected from the group consisting of *Gallus gallus, Meleagris gallopavo, Anas platyrhynchos, Bos taurus, Sus scrofa, Ovis aries, Salmo salar, Thunnus thynnus, Gadus morhua, Homarus americanus, Litopenaeus setiferus, Oncorhynchus mykiss,* and *Oreochromis niloticus.*

Embodiment I-21. The method as in any one of embodiments I-1 to I-20, wherein adding the at least one filter aid comprises flowing media containing the at least one filter aid.

Embodiment I-22. The method as in any one of embodiments I-1 to I-21, wherein the at least one filter aid is added at the same time, sequentially, alternately, or in any relevant order thereto.

Embodiment I-23. The method as in any one of embodiments I-1 to I-22, wherein adding the plurality of cells comprises flowing media containing the plurality of cells.

Embodiment I-24. The method as in any one of embodiments I-1 to I-23, wherein the plurality of cells are added at the same time, sequentially, alternately, or in any relevant order thereto.

Embodiment I-25. The method as in any one of embodiments I-1 to I-24, wherein the filter cake is edible.

Embodiment I-26. The method as in any one of embodiments I-1 to I-25, further comprising harvesting the cells or the tissues produced therefrom, from the filter cake.

Embodiment I-27. The method as in any one of embodiments I-1 to I-26, wherein the media comprises GRAS-ingredients, optionally only GRAS-ingredients.

Embodiment I-28. The method as in any one of embodiments I-1 to I-27, wherein the cells are cultivated into a tissue intended for human consumption.

Embodiment I-29. The method as in any one of embodiments I-1 to I-28, wherein the cells are cultivated into a tissue intended for therapeutic purposes.

Embodiment I-30. A system for cultivating cells and cell biomass, the system comprising:
  a) a filter chamber comprising at least one inlet and at least one outlet;
  b) at least one filter support located within the filter chamber; and
  c) a filter cake located on the filter support, wherein the filter cake comprises at least one filter aid and a plurality of cells.

Embodiment I-31. The system of embodiment I-30, wherein the filter cake comprises at least two different cell types.

Embodiment I-32. The system as in any one of embodiments 1-30 to I-31, wherein the cells are selected from metazoan cells.

Embodiment I-33. The system as in any one of embodiments 1-30 to I-32, wherein the cells are selected from the group consisting of skeletal muscle cells, stem cells, pluripotent stem cells, embryonic stem cells, induced pluripotent stem cells, fibroblasts, myoblasts, somatic cells, extraembryonic cells, myocytes, satellite cells, side population cells, muscle derived stem cells, mesenchymal stem cells, myogenic pericytes, mesoangioblasts, and adipocytes.

Embodiment I-34. The system as in any one of embodiments 1-30 to I-33, wherein the cells are co-cultures of fibroblast and myoblasts at a ratio of between about 95F:5M to 5F:95M.

Embodiment I-35. The system as in any one of embodiments 1-30 to I-34, wherein the cells are from a species of poultry, game, aquatic, or livestock.

Embodiment I-36. The system as in any one of embodiments 1-30 to I-35, wherein the cells are selected from the group consisting of *Gallus gallus, Meleagris gallopavo, Anas platyrhynchos, Bos taurus, Sus scrofa, Ovis aries, Salmo salar, Thunnus thynnus, Gadus morhua, Homarus americanus, Litopenaeus setiferus, Oncorhynchus mykiss,* and *Oreochromis niloticus.*

Embodiment I-37. The system as in any one of embodiments 1-30 to I-36, wherein the filter chamber is in fluid communication with at least one reservoir containing cells.

Embodiment I-38. The system as in any one of embodiments 1-30 to I-37, wherein the filter chamber is in fluid communication with at least one reservoir containing the filter aid.

Embodiment I-39. The system as in any one of embodiments 1-30 to I-38, wherein the temperature of the filter chamber is maintained at between about 10° C.-about 45° C.

Embodiment I-40. The system as in any one of embodiments 1-30 to I-39, wherein the flow rate between the inlet and the outlet is between about 1 L/min-1000 L/min.

Embodiment I-41. The system as in any one of embodiments 1-30 to I-40, wherein the pressure between the inlet and the outlet is between about 0.1 bar-5.0 bar.

Embodiment I-42. The system as in any one of embodiments 1-30 to I-41, wherein the filter aid is added to the filter support at between about 25 g/m 2-12000 g/m$^2$, 50 g/m$^2$-6000 g/m$^2$, 100 g/m$^2$-3000 g/m$^2$, 200 g/m$^2$-1500 g/m$^2$, or 400 g/m$^2$-750 g/m$^2$.

Embodiment I-43. The system as in any one of embodiments 1-30 to I-42, wherein the filter chamber has a size of between about 5 liter-25,000 liters.

Embodiment I-44. The system as in any one of embodiments 1-30 to I-43, wherein the filter support has surface area of between about 1 meter 2-2000 meter$^2$.

Embodiment I-45. The system as in any one of embodiments 1-30 to I-44, wherein the filter cake comprises two cell types in alternating layers.

Embodiment I-46. The method as in any one of embodiments I-1 to I-29, wherein the filter cake comprises two cell types in alternating layers.

Embodiment II-1. A method for optimizing the cultivation of cells and cell biomass, the method comprising:
 a) providing a filter support;
 b) adding at least one filter aid to the filter support, wherein the at least one filter aid is compressible;
 c) adding a plurality of cells to the filter aid, wherein the cells and the filter aid together comprise a filter cake;
 d) compressing the filter cake; and
 e) culturing the cells in the filter cake.

Embodiment II-2. The method of embodiment II-1, comprising harvesting the cells and the tissues produced therefrom.

Embodiment II-3. The method of embodiment II-1, wherein a meat product is thereby generated.

Embodiment II-4. The method of embodiment II-1, comprising compressing the filter cake by varying one or more of flow rate and pressure.

Embodiment II-5. The method of embodiment II-1, wherein the filter cake is edible.

Embodiment II-6. The method of embodiment II-1, wherein the at least one filter aid is compressible.

Embodiment II-7. The method of embodiment II-1, wherein the at least one filter aid is edible.

Embodiment II-8. The method of embodiment II-1, wherein the at least one filter aid is selected from the group consisting of cellulose, starch, diatomaceous earth, perlites, active charcoal, plant fibers, fungal mycella, algae, and organic fibers.

Embodiment II-9. The method of embodiment II-1, wherein the organic fibers comprise a length of between about 1 μm-20 μm, 20 μm-50 μm, 50 μm-80 μm, 80 μm-110 μm, 110 μm-140 μm, 140 μm-170 μm, 170 μm-200 μm, 200 μm-230 μm, 230 μm-260 μm, 260 μm-290 μm, or 290 μm-320 μM.

Embodiment II-10. The method of embodiment II-1, wherein the organic fiber has a fiver titer of between about 0.01 dtex-120 dtex, 0.05 dtex-60 dtex, 0.1 dtex-30 dtex, 0.2 dtex-15 dtex, or 0.5 dtex-5 detx.

Embodiment II-11. The method of embodiment II-1, wherein the at least one filter aid is added to the filter support at between about 25 g/m$^2$-12000 g/m$^2$, 50 g/m$^2$-6000 g/m$^2$, 100 g/m$^2$-3000 g/m$^2$, 200 g/m$^2$-1500 g/m$^2$, or 400 g/m$^2$-750 g/m$^2$.

Embodiment II-12. The method of embodiment II-1, wherein the filter support is selected from the group consisting of a horizontal filter, vertical filter, plate filter, plate press filter, mash filter, cloth filter, and a candle filter.

Embodiment II-13. The method of embodiment II-1, wherein the temperature is maintained at between about 10° C. to about 45° C.

Embodiment II-14. The method of embodiment II-1, wherein the cells are from a species of poultry, game, aquatic, or livestock.

Embodiment II-15. The method of embodiment II-1, wherein the cells are selected from the group consisting of *Gallus gallus*, *Meleagris gallopavo*, *Anas platyrhynchos*, *Bos taurus*, *Sus scrofa*, *Ovis aries*, *Salmo salar*, *Thunnus thynnus*, *Gadus morhua*, *Homarus americanus*, *Litopenaeus setiferus*, *Oncorhynchus mykiss*, and *Oreochromis niloticus*.

Embodiment II-16. The method of embodiment II-1, wherein adding the at least one filter aid comprises flowing media containing the at least one filter aid.

Embodiment II-17. The method of embodiment II-1, wherein adding the plurality of cells comprises flowing media containing the plurality of cells.

Embodiment II-18. A system for cultivating cells and cell biomass, the system comprising:
 a) a filter chamber comprising at least one inlet and at least one outlet;
 b) at least one filter support located within the filter chamber; and
 c) a filter cake located on the filter support, wherein the filter cake is compressible, and comprises at least one filter aid and a plurality of cells.

Embodiment II-19. The system of embodiment II-18, wherein the filter chamber is in fluid communication with at least one reservoir containing cells.

Embodiment II-20. The system of embodiment II-18, wherein the filter chamber is in fluid communication with at least one reservoir containing the filter aid.

Embodiment III-1. A method for optimizing the cultivation of cells and cell biomass, the method comprising:
 a) providing a filter support;
 b) adding at least one filter aid to the filter support;
 c) adding a plurality of cells to the filter aid, wherein the cells and the filter aid together comprise a filter cake; and
 d) growing the cells into a cell biomass in the filter cake, wherein the filter cake is at least partially compressible.

Embodiment III-2. The method of embodiment III-1, wherein the cell biomass is a meat product.

Embodiment III-3. The method of embodiment III-1, comprising compressing or decompressing the filter cake by varying one or more of flow rate and pressure.

Embodiment III-4. The method of embodiment III-1, wherein the filter cake is edible.

Embodiment III-5. The method of embodiment III-1, wherein the at least one filter aid is at least partially compressible.

Embodiment III-6. The method of embodiment III-1, wherein the at least one filter aid is edible or degradable.

Embodiment III-7. The method of embodiment III-1, wherein the filter aid comprises at least one compressible filter aid and one non-compressible filter aid.

Embodiment III-8. The method of embodiment III-1, wherein the organic fibers comprise a length of between about 1 μm-20 μm, 20 μm-50 μm, 50 μm-80 μm, 80 μm-110 μm, 110 μm-140 μm, 140 μm-170 μm, 170 μm-200 μm, 200 μm-230 μm, 230 μm-260 μm, 260 μm-290 μm, or 290 μm-320 μM.

Embodiment III-9. The method of embodiment III-1, wherein the organic fiber has a fiver titer of between about 0.01 dtex-120 dtex, 0.05 dtex-60 dtex, 0.1 dtex-30 dtex, 0.2 dtex-15 dtex, or 0.5 dtex-5 detx.

Embodiment III-10. The method of embodiment III-1, wherein the at least one filter aid is added to the filter support at between about 25 g/m²-12000 g/m², 50 g/m²-6000 g/m², 100 g/m²-3000 g/m², 200 g/m²-1500 g/m², or 400 g/m²-750 g/m².

Embodiment III-11. The method of embodiment III-1, wherein the filter support is contained in a horizontal filter, vertical filter, plate filter, plate press filter, mash filter, cloth filter, mass filter, or candle filter.

Embodiment III-12. The method of embodiment III-1, wherein the temperature is maintained at between about 10° C. to about 45° C.

Embodiment III-13. The method of embodiment III-1, wherein the cells are from a species of poultry, game, aquatic, or livestock.

Embodiment III-14. A method for establishing perfusion through a growing cell biomass, the method comprising:
a) seeding cells on an at least partially compressible filter aid;
b) compressing the cells, the at least partially compressible filter aid, or both;
c) flowing media through the at least partially compressible filter aid to grow the cells into a cell biomass, whereby growth reduces perfusion over time; and
d) decompressing the cells, the at least partially compressible filter aid, or both, to increase perfusion of media.

Embodiment III-15. The method of embodiment III-14, wherein the cell biomass is compressed by a fluid pressure or flow of the media.

Embodiment III-16. The method of embodiment III-14, wherein the cell culture media provides nutrients and oxygenation to promote cell growth.

Embodiment III-17. The method of embodiment III-14, wherein the cell biomass is decompressed with a relief valve, a lower pressure media flow, flow reduction of the media, or some combination thereof.

Embodiment III-18. The method of embodiment III-14, wherein the cell biomass, its substrate, or both are decompressed proportionally to the growth of the cell mass, whereby perfusion is stabilized.

Embodiment III-19. The method of embodiment III-14, wherein the cell biomass, the at least partially compressible filter aid, or both cycle between a compressed state and a decompressed state at a pulsing frequency.

Embodiment III-20. The method of embodiment III-19, wherein the pulsing frequency is between 20 seconds and 20 minutes.

What is claimed is:

1. A cell-based meat product comprising:
an edible filter aid comprising a plurality of discrete and separate particles or fibers; and
a plurality of cells, the plurality of cells being derived from a non-human animal species intended for human or non-human dietary consumption;
wherein cells of the plurality of cells are embedded within the edible filter aid.

2. The cell-based meat product as in claim 1, wherein the edible filter aid comprises one or more of fungal mycella, plant fibers, or cellulose.

3. The cell-based meat product as in claim 1, wherein the edible filter aid comprise one or more of algae, plant fibers, starch particles, or plant-based proteins.

4. The cell-based meat product as in claim 1, wherein the edible filter aid is hollow.

5. The cell-based meat product as in claim 1, wherein the edible filter aid is degradable.

6. The cell-based meat product as in claim 5, wherein the edible filter aid is configured to be at least partially degraded by cell secretions.

7. The cell-based meat product as in claim 1, wherein the edible filter aid is compressible.

8. The cell-based meat product as in claim 1, wherein cells of the plurality of cells adhere to the edible filter aid.

9. The cell-based meat product as in claim 1, wherein the plurality of cells comprises:
cells of a first type comprising one of myoblasts, adipocytes, or fibroblasts; and
cells of a second type comprising another of myoblasts, adipocytes, or fibroblasts.

10. The cell-based meat product as in claim 9, wherein the cells of the first type are arranged in a first layer and the cells of the second type are arranged in an adjacent layer.

11. A cell biomass comprising:
an edible filter aid comprising a plurality of discrete and separate particles or fibers; and
a plurality of cells grown about the edible filter aid, the plurality of cells being derived from a non-human animal species intended for human or non-human dietary consumption.

12. The cell biomass of claim 11, wherein the edible filter aid comprises one or more of fungal mycella, plant fibers, or cellulose.

13. The cell biomass of claim 11, wherein the cell biomass is a meat product for human dietary consumption.

14. The cell biomass of claim 11, wherein the edible filter aid comprise one or more of algae, plant fibers, starch particles, or plant-based proteins.

15. The cell biomass of claim 11, wherein the edible filter aid is degradable.

16. The cell biomass of claim 11, wherein the plurality of cells comprise cells from a species of poultry, game, aquatic, or livestock.

17. The cell biomass of claim 11, wherein the edible filter aid is hollow.

18. The cell biomass of claim 11, wherein the edible filter aid comprises fibers with a fiber titer of between about 0.01 dtex-about 120 dtex, about 0.05 dtex-about 60 dtex, about 0.1 dtex-about 30 dtex, about 0.2 dtex-about 15 dtex, or about 0.5 dtex-about 5 dtex.

19. The cell biomass of claim 11, wherein the edible filter aid comprises fibers of a length of between about 1 μm-about 20 μm, about 20 μm-about 50 μm, about 50 μm-about 80 μm, about 80 μm-about 110 μm, about 110 μm-about 140 μm, about 140 μm-about 170 μm, about 170 μm-about 200 μm, about 200 μm-about 230 μm, about 230 μm-about 260 μm, about 260 μm-about 290 μm, or about 290 μm-about 320 μm.

20. The cell biomass of claim 11, wherein cells of the plurality of cells adhere to the edible filter aid.

* * * * *